US010849643B2

(12) United States Patent
Castillo et al.

(10) Patent No.: US 10,849,643 B2
(45) Date of Patent: Dec. 1, 2020

(54) METHODS AND SYSTEMS FOR INSERTION AND FIXATION OF IMPLANTABLE DEVICES

(71) Applicant: Nalu Medical, Inc., Carlsbad, CA (US)

(72) Inventors: Andre Castillo, Encinitas, CA (US); Christopher Linden, Vista, CA (US); Lee Fason Hartley, Carlsbad, CA (US); Lakshmi Narayan Mishra, Carlsbad, CA (US); James C. Makous, Encinitas, CA (US)

(73) Assignee: Nalu Medical, Inc., Carlsbad, CA (US)

( * ) Notice: Subject to any disclaimer, the term of this patent is extended or adjusted under 35 U.S.C. 154(b) by 146 days.

(21) Appl. No.: 16/120,139

(22) Filed: Aug. 31, 2018

(65) Prior Publication Data
US 2018/0368875 A1 Dec. 27, 2018

Related U.S. Application Data

(63) Continuation of application No. PCT/US2017/034553, filed on May 25, 2017.
(Continued)

(51) Int. Cl.
*A61B 17/32* (2006.01)
*A61N 1/375* (2006.01)
(Continued)

(52) U.S. Cl.
CPC ...... *A61B 17/320016* (2013.01); *A61B 17/32* (2013.01); *A61B 17/3468* (2013.01);
(Continued)

(58) Field of Classification Search
CPC .... A61B 17/320016; A61B 2017/0414; A61B 2017/320044; A61B 2017/320052;
(Continued)

(56) References Cited

U.S. PATENT DOCUMENTS 5,827,311 A * 10/1998 Berelsman ..... A61B 17/320036
606/167
5,908,433 A 6/1999 Eager et al.
(Continued)

FOREIGN PATENT DOCUMENTS

EP 1342454 A1 9/2003
WO WO-2014205129 A1 12/2014
(Continued)

OTHER PUBLICATIONS

PCT/US2017/034553 International Search Report and Written Opinion dated Oct. 10, 2017.
(Continued)

*Primary Examiner* — Katrina M Stransky
(74) *Attorney, Agent, or Firm* — Wilson Sonsini Goodrich and Rosati, P.C.

(57) ABSTRACT

A tunneling tool for forming a tissue channel and/or pocket beneath a portion of skin along a body comprises a distal end having a tunneling member and a guide. The tunneling member is configured for forming the tissue channel and/or pocket beneath the portion of skin while the guide remains above the skin and indicates the location of at least a portion of the tunneling member. An anchor for securing an elongate device to body tissue comprises an anchor body configured to receive the elongate device; a mechanism configured to removably attach the anchor body to the elongate device so as to resist movement of the elongate device in relation to the anchor body; and at least one tissue engagement element configured to assist in attaching the anchor body to the body tissue.

28 Claims, 24 Drawing Sheets

Related U.S. Application Data

(60) Provisional application No. 62/341,418, filed on May 25, 2016.

(51) Int. Cl.
*A61B 17/34* (2006.01)
*A61B 17/04* (2006.01)
*A61B 90/00* (2016.01)

(52) U.S. Cl.
CPC .. *A61N 1/37518* (2017.08); *A61B 2017/0414* (2013.01); *A61B 2017/320044* (2013.01); *A61B 2017/320052* (2013.01); *A61B 2017/320056* (2013.01); *A61B 2090/0811* (2016.02)

(58) Field of Classification Search
CPC ........ A61B 2017/320056; A61B 17/32; A61B 17/3468; A61B 5/042; A61N 1/37518; A61N 1/059
See application file for complete search history.

(56) References Cited

U.S. PATENT DOCUMENTS

| | | | |
|---|---|---|---|
| 6,482,152 B2 | 11/2002 | Kim et al. | |
| 8,252,011 B1* | 8/2012 | Forrester | A61B 17/320016 606/167 |
| 10,238,872 B2 | 3/2019 | Pivonka et al. | |
| 10,335,596 B2 | 7/2019 | Yakovlev et al. | |
| 2006/0190021 A1* | 8/2006 | Hausman | A61B 17/320016 606/167 |
| 2008/0045989 A1* | 2/2008 | Welborn | A61B 17/320036 606/170 |
| 2008/0195128 A1* | 8/2008 | Orbay | A61B 1/00048 606/170 |
| 2008/0214992 A1 | 9/2008 | Haarala et al. | |
| 2011/0034886 A1 | 2/2011 | Elbe et al. | |
| 2016/0015411 A1 | 1/2016 | Keller et al. | |
| 2016/0113671 A1 | 4/2016 | Berger et al. | |
| 2016/0331956 A1 | 11/2016 | Yakovlev et al. | |
| 2018/0028824 A1 | 2/2018 | Pivonka et al. | |
| 2018/0256906 A1 | 9/2018 | Pivonka et al. | |
| 2019/0001139 A1 | 1/2019 | Mishra et al. | |
| 2019/0009097 A1 | 1/2019 | Hartley et al. | |
| 2019/0151659 A1 | 5/2019 | Mishra et al. | |
| 2019/0269913 A1 | 9/2019 | Pivonka et al. | |
| 2019/0374776 A1 | 12/2019 | Mishra et al. | |
| 2020/0101291 A1 | 4/2020 | Yakovlev et al. | |
| 2020/0139138 A1 | 5/2020 | Sit et al. | |

FOREIGN PATENT DOCUMENTS

| | | |
|---|---|---|
| WO | WO 2015/081231 A1 * | 6/2015 |
| WO | WO-2015139053 A1 | 9/2015 |
| WO | WO-2015196164 | 12/2015 |
| WO | WO-2016127130 A1 | 8/2016 |
| WO | WO-2017044904 A1 | 3/2017 |
| WO | WO-2017142948 A1 | 8/2017 |
| WO | WO-2017165410 A1 | 9/2017 |
| WO | WO-2017205675 A1 | 11/2017 |
| WO | WO-2018017463 A1 | 1/2018 |
| WO | WO-2018126062 A1 | 7/2018 |
| WO | WO-2018156953 A1 | 8/2018 |
| WO | WO-2018208992 A1 | 11/2018 |

OTHER PUBLICATIONS

Cardador. Review of Existing, Mounted Targeting Devices for Distal Locking of Intramedullary Nails. "Practice of Intramedullary Locked Nails" pp. 265-270 (2006).
EP17803621.8 Extended Search Report dated Oct. 30, 2019.

\* cited by examiner

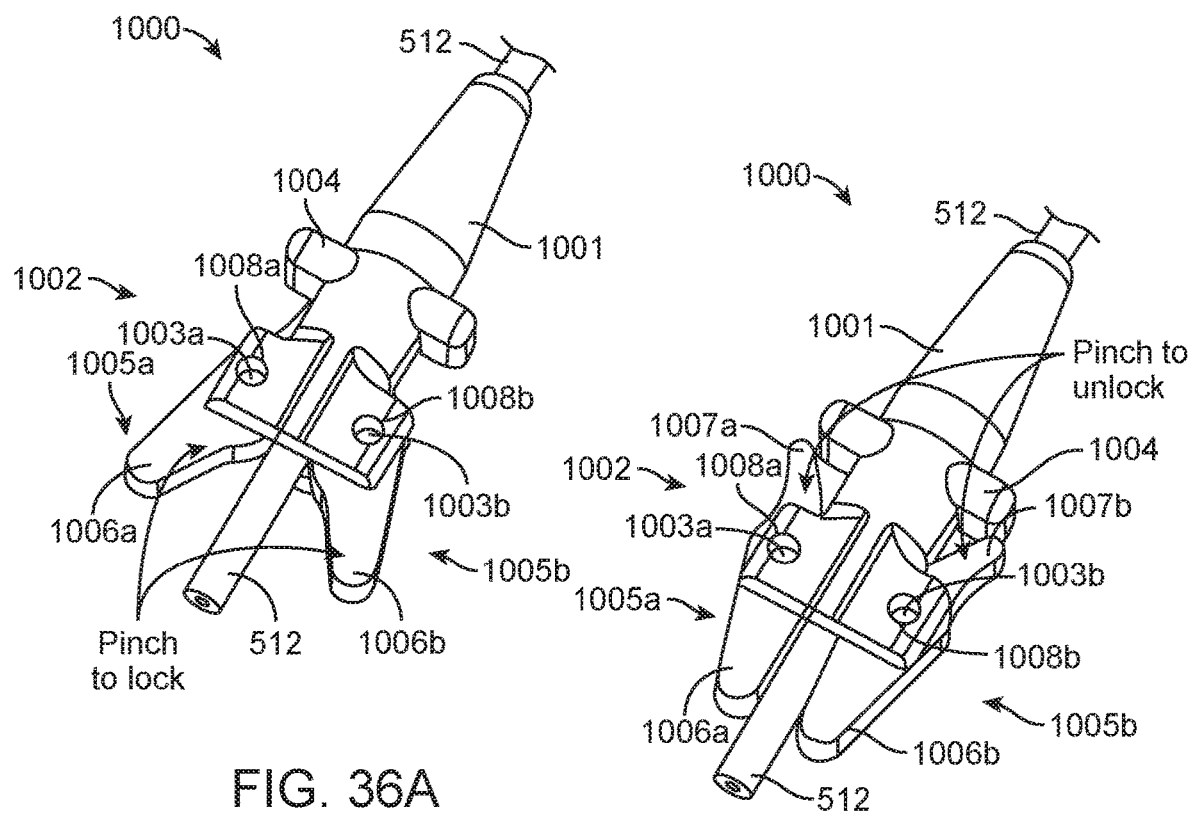
FIG. 36A
FIG. 36B
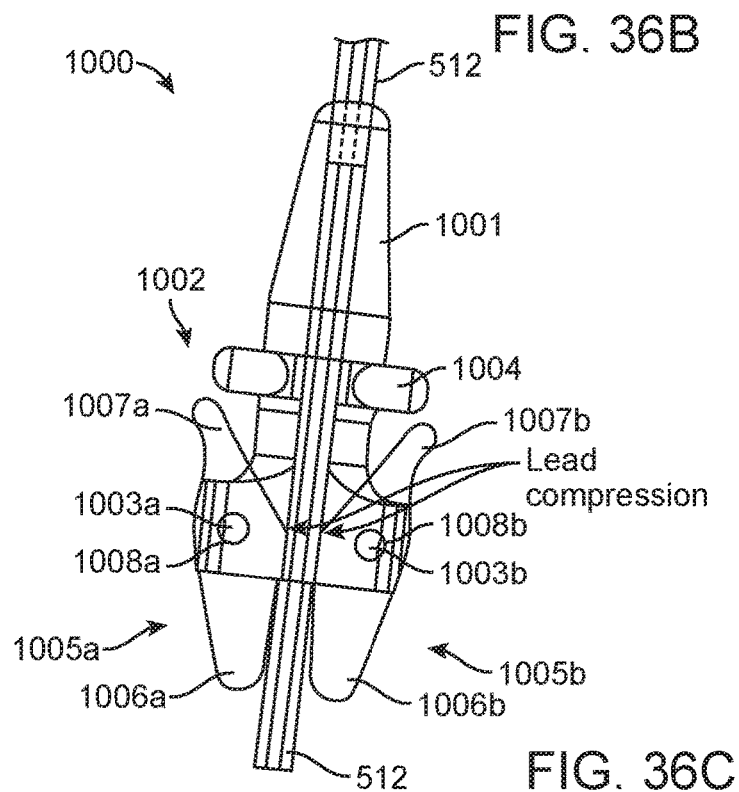
FIG. 36C

Locked

Unlocked

METHODS AND SYSTEMS FOR INSERTION AND FIXATION OF IMPLANTABLE DEVICES

CROSS REFERENCE

This application is a continuation of PCT Application No. PCT/US2017/034553, filed May 25, 2017, which claims priority to U.S. Provisional Application No. 62/341,418, filed May 25, 2016, the content of which is incorporated herein by reference in its entirety for all purposes.

BACKGROUND OF THE INVENTION

This invention relates generally to the field of systems and methods for inserting and fixating implantable devices within the body of a patient. Particularly, this invention relates to surgical tools for assisting in the delivery of various implantables and to anchors for fixating various implantables within the body.

Various devices and other implantables are designed to be implanted subcutaneously or subdermally within a patient's body. Such positioning is considered under the skin, or in the layer of skin directly below the dermis and epidermis. To implant such a device, an incision can be made down to the subcutaneous layer (subcutis) of the skin. A dermal elevator, a widely used medical instrument, separates the subcutis and the fascia, creating the pocket in which the implant will be inserted. After the implant is placed, the incision is stitched shut. Surgical tape is often applied to minimize movement while the skin fuses around the implant.

However, such open procedures are less favorable in comparison to minimally invasive techniques. Minimally invasive techniques allow smaller incisions, shorter procedure time, quicker recovery time, less pain and less scarring. The present invention provides surgical tools for delivery of various subcutaneous implantables in a minimally invasive manner. In particular, the present invention provides tools for precise delivery of small implantables.

Other implantable devices, such as leads, are designed to be implanted in various locations throughout the body, such as beyond the subcutaneous layer. These devices are typically held in place by suturing of the device to the surrounding tissue. However, surgeons have varying suturing techniques, and there can be wide variation in anchoring success. Poor anchoring techniques may cause damage to the lead or early displacement from incorrect suture tension. The present invention provides anchoring devices to assist in desired anchoring of implantable devices, such as leads.

SUMMARY OF THE INVENTION

According to one aspect of the present inventive concepts, a tunneling tool for forming a tissue channel and/or pocket beneath a portion of skin along a body comprises a distal end having a tunneling member and a guide. The tunneling member is configured for forming the tissue channel and/or pocket beneath the portion of skin while the guide remains above the skin and indicates the location of at least a portion of the tunneling member.

In some embodiments, the guide is positioned above the tunneling member such that the guide remains above the skin while the tunneling member enters subcutaneous tissue.

In some embodiments, the guide is aligned with the tunneling member such that a user can determine the location of the tunneling member based on the location of the guide.

In some embodiments, the guide comprises a first shape, the tunneling member comprises a second shape, and the first shape is similar to the second shape. The first shape can be the same as the second shape.

In some embodiments, the guide comprises a first width, the tunneling member comprises a second width, and the first width is similar to the second width. The first width can be the same as the second width.

In some embodiments, the guide comprises a first width, the tunneling member comprises a second width, and the first width is dissimilar to the second width. The first width can be less than the second width.

In some embodiments, the guide comprises a first length, the tunneling member comprises a second length, and the first length is similar to the second length. The first length can be the same as the second length.

In some embodiments, the guide comprises a first length, the tunneling member comprises a second length, and the first length is dissimilar to the second length. The first length can be shorter than the second length. The tunneling member can be configured to pass through the skin into the subcutaneous tissue without interference from the guide.

In some embodiments, the guide is positioned parallel to the tunneling member, and the position of the guide indicates a position of the tunneling member.

In some embodiments, the guide includes one or more markings. The tunneling member can comprise a distal tip, and the one or more markings can indicate a distance between the markings and the distal tip of the tunneling member. The one or more markings can be spaced at regular increments. The one or more markings can comprise two or more markings that are spaced approximately 0.5 cm, 1.0 cm, 1.5 cm and/or 2.0 cm apart. The one or more markings can be spaced at irregular increments.

In some embodiments, the tunneling tool comprises a shaft. The shaft can comprise a curved shape such that the proximal end is positioned higher than the distal end. The curved shape of the shaft can provide clearance between a hand of a user grasping the tunneling tool and a surface of the skin, such as when the tunneling member is inserted into the skin.

In some embodiments, a distance between the tunneling member and the guide is fixed.

In some embodiments, a distance between the tunneling member and the guide is adjustable.

In some embodiments, the tunneling member comprises a distal end including a mount, and the mount is configured to rotate about the distal end. The mount can rotate about the distal end between a stored position and a receiving position. The stored position can comprise the mount disposed within the tunneling member. The receiving position can comprise the mount extending from the tunneling member.

In some embodiments, the tunneling member comprises a distal tip. The distal tip can comprise a round shape and/or a pointed shape. The pointed distal tip can comprise a blade.

In some embodiments, the tunneling tool comprises a proximal portion including a handle.

In some embodiments, the guide comprises an open window.

In some embodiments, the tunneling tool comprises a storage receptacle for receiving and storing the guide.

In some embodiments, the tunneling member comprises an enlarged distal end.

According to another aspect of the present inventive concepts, an anchor for securing an elongate device to body tissue, the anchor comprises: an anchor body configured to receive the elongate device; a mechanism configured to removably attach the anchor body to the elongate device so as to resist movement of the elongate device in relation to the anchor body; and at least one tissue engagement element configured to assist in attaching the anchor body to the body tissue.

In some embodiments, the mechanism comprises a first portion and a second portion of the anchor body. The first portion can comprise a base with a lumen, and the lumen can be configured to receive the elongate device therethrough. The first portion can comprise a base, and the second portion can comprise a locking member constructed and arranged to mate with the base. The locking member can comprise a protrusion and a grip. The locking member protrusion can comprise one or more teeth. The base can be configured to receive the protrusion, such that a pressure applied to the grip forces the protrusion into the base, and the protrusion locks the elongate device in place. The mechanism can be constructed and arranged to prevent overclamping of the elongate device.

In some embodiments, the at least one tissue engagement element comprises one or more elements of the anchor body that are configured to prevent movement of the anchor body relative to the body tissue, such as to avoid suturing.

In some embodiments, the mechanism comprises a portion of the anchor body that includes a material configured to increase a retention force on the elongate device. The anchor body material can comprise a material having a higher coefficient of friction. The anchor body material can comprise a soft durometer silicone. The anchor body material can comprise a material with a textured surface.

In some embodiments, the mechanism comprises one or more engagement elements of the anchor body configured to engage the elongate device. The one or more engagement elements can comprise barbs. The one or more engagement elements can be constructed and arranged as unidirectional gripping elements. The one or more engagement elements can be constructed and arranged as bidirectional gripping elements.

In some embodiments, the anchor body comprises a first portion and a second portion, such that the first portion and second portion are constructed and arranged to mate with the other. The mechanism can comprise the first portion and the second portion, and the first portion and the second portion can be configured to lock onto the elongate device. The mechanism can comprise the first portion and the second portion, and the first portion can comprise a first lever arm and a first jaw and the second portion can comprise a second lever arm and a second jaw. The first lever arm and the first jaw can be integrated into a single component. The first lever arm and the first jaw can be separate components. The first portion and the second portion can mate with the other, such that the first and second lever arms can be configured to align and the first and second jaws are configured to align. The aligned lever arms and the aligned jaws can comprise a lumen configured to receive the elongate device.

In some embodiments, the mechanism comprises two or more sets of lever arms corresponding to two or more sets of jaws.

In some embodiments, the anchor body comprises a first portion and a second portion, and the first portion and second portion are constructed and arranged to mate with the other to form a lumen therebetween, and the mechanism comprises the lumen. The mechanism can comprise a locking member configured to surround at least a portion of the anchor body, such that the locking member can hold the first portion and the second portion in the mated position. The mechanism can further comprise a sleeve, the lumen can be constructed and arranged to receive the sleeve, and the sleeve can be constructed and arranged to receive the elongate device. The sleeve can comprise a surface configured to increase a retention force on the elongate device.

In some embodiments, the mechanism comprises a first portion and a second portion of the anchor body, and the first portion and the second portion are constructed and arranged to translate in relation to the other. The translation of the first portion and the second portion can secure the anchor onto the elongate device. The first portion can comprise a base with a lumen and the second portion can comprise a cover. The lumen can be configured to receive the elongate device. The cover can be constructed and arranged to extend over at least a portion of the base. The cover can comprise two or more holes, and the two or more holes can align with the lumen of the base to receive the elongate device.

In some embodiments, the mechanism comprises at least one surface portion of the anchor body configured to increase a retention force applied to the elongate device.

In some embodiments, the tissue engagement element comprises one or more elements of the anchor body configured to prevent a movement of the anchor relative to the body tissue. The tissue engagement elements can be configured to avoid suturing of the anchor to tissue. The anchor body can comprise a spring that controls the clamping force of the tissue engagement elements on tissue. The spring can comprise a compression spring.

In some embodiments, anchor body comprises a base with a first lumen therethrough and at least one off-set portion with a second lumen therethrough, and the mechanism comprises the base, the first lumen and the second lumen. The first lumen and the second lumen can be constructed and arranged to receive the elongate device. The first lumen and the second lumen can be configured to align via a movement of the off-set portion, such that the elongate device can be advanced through the first lumen and the second lumen. The first lumen and the second lumen can be configured to misalign via a movement of the off-set portion, such that the position of the elongate device is maintained.

In some embodiments, the mechanism comprises two cams which rotate to engage the elongate device.

In some embodiments, the mechanism comprises two rotatable arms and an O-ring, and the O-ring is positioned around the two rotatable arms to engage the arms to the elongate device.

In some embodiments, the mechanism comprises a tortuous path for receiving and engaging the elongate device. The tortuous path can comprise a pathway of a conduit, a pathway of a tortuous element, and/or a pathway of the anchor body.

In some embodiments, the mechanism comprises an inner body and outer body of the anchor body, the inner body comprises a first lumen and the outer body comprises a second lumen, the first lumen and the second lumen are each configured to receive the elongate device, and rotation of the inner body engages the elongate device. The anchor can further comprise a tool configured to engage and rotate the inner body.

In some embodiments, the anchor further comprises a nose cone configured to relieve strain applied to the elongate device by flexion between the elongate device and the anchor.

In some embodiments, the anchor further comprises at least one suture retention ring.

In some embodiments, the anchor comprises a surface configured to increase retention force with the elongate device.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth herein. An understanding of the features and advantages of the present invention will be obtained by reference to the following detailed description that sets forth illustrative embodiments, in which the principles of the invention are utilized, and the accompanying drawings of which:

FIGS. 36A-C are two perspective views, and a top transparent view, respectively, of an anchor which locks onto an elongate device.

DETAILED DESCRIPTION OF THE INVENTION

Specific embodiments of the disclosed device, system, and method will now be described with reference to the drawings. Nothing in this detailed description is intended to imply that any particular component, feature, or step is essential to the invention.

Tunneling Tools

Figure 1A:
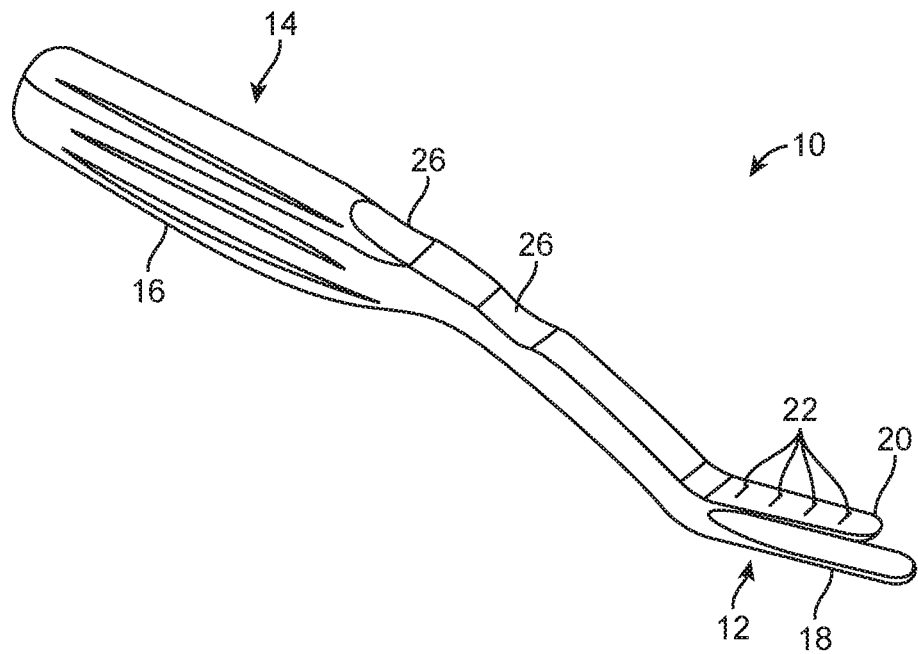
FIG. 1A is a perspective illustration of an embodiment of a tunneling tool wherein the tunneling tool is configured for tunneling into subcutaneous tissue structures within the body.

FIG. 1A is a perspective illustration of an embodiment of a tunneling tool 10, wherein the tunneling tool 10 is configured for tunneling into subcutaneous tissue structures within the body of a patient to form a tissue channel or pocket. The tunneling tool 10 has a distal end 12 and a proximal end 14. In this embodiment, the proximal end 14 includes a handle 16 for gripping by a user, such as a physician or surgeon. Typically, the handle 16 is ergonomic and provides enhanced gross motor control of the tool 10. In this embodiment, the distal end 12 includes a tunneling member 18 which is configured to pass through the surface of the skin and into the subcutaneous tissue structures therein. The length of insertion can be indicated by a guide 20 which is disposed above the tunneling member 18 and is configured to remain outside and above the skin while the tunneling member enters the subcutaneous tissue. The guide 20 is aligned with the tunneling member 18 so that the user (e.g. an implanting clinician) is able to determine the location of the tunneling member 18 beneath the skin based on the location of the guide 20. In some embodiments, the guide 20 has a shape which matches, or at least is similar to, the tunneling member 18. In some embodiments, the guide 20 has a width and/or length which matches, or at least is similar to, the width and/or length, respectively, of tunneling member 18. In some embodiments, the guide 20 has a shape, width, and/or length with is dissimilar to tunneling member 18's shape, width, and/or length, respectively. In some embodiments, the guide 20 is oriented substantially parallel to the tunneling member. In each of these instances, the position of the guide 20 above the skin can help the user visualize the position of the tunneling member 18 thereunder. It may be appreciated that in some embodiments, the guide 20 has a different length (e.g. a shorter length) than the tunneling member 18, such as the shorter length illustrated in FIG. 1A. In other words, the distal tip of the guide 20 is recessed from the distal tip of the tunneling member 18. This shorter length allows the tunneling member 18 to pass through the skin and into the subcutaneous tissue without interference by the guide 20.

It may be appreciated that, in some embodiments, the guide 20 includes one or more length indication markings 22. The length marking(s) 22 may indicate any suitable increment of measure. In some embodiments, two or more length indication markings 22 are present, each spaced 1-1.5 cm apart. FIG. 1A illustrates four length indication markings 22, each spaced 1 cm apart. However, it may be appreciated that one, two, three, four, five, six, seven, eight, nine, ten or more indication length markings may be present. Likewise, such markings 22 can be spaced apart by approximately 0.5 cm, 1 cm. 1.5 cm, or 2 cm, to name a few. Further, such markings 22 may be regularly or irregularly spaced. The guide 20 is aligned with the tunneling member 18 so that each marking 22 correlates to (e.g. indicates to a user) a distance between the marking 22 and the distal tip of the tunneling member 18. Thus, as the tunneling member 18 tunnels through the subcutaneous tissue of the patient, creating a tissue channel, the user is continually aware of the length of the channel by correlating the edge of the skin at the entry point with the markings 22. Consequently, the user is able to determine the precise length of the channel.

Creation of the tissue channel typically involves pushing the tool 10 forward so that the tunneling member 18 bluntly dissects the subcutaneous tissue. The handle 16 enables effective force transfer during the blunt dissection. Likewise, in some embodiments, the tool 10 further includes one or more grip indents 26. These indents 26 provide additional surfaces to transfer force and also reduce any possibility of grip slippage. The indents 26 also provide for alternate grip positions to optimize user comfort and fine motor control.

Figure 1B:
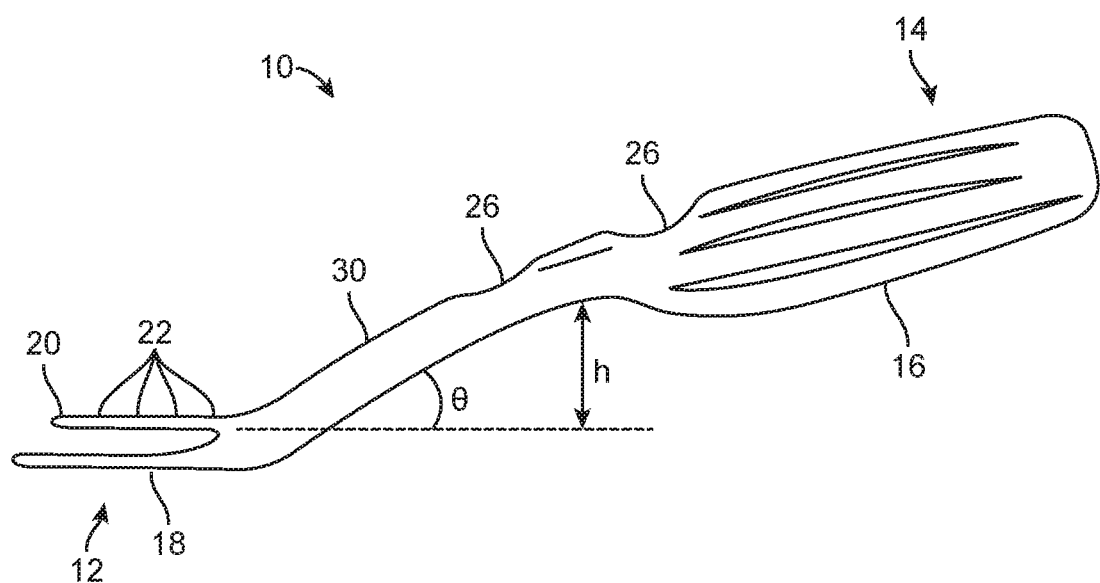
FIG. 1B provides a side view illustration of the tunneling tool of FIG. 1A.

FIG. 1B provides a side view illustration of the tunneling tool 10 of FIG. 1A. As shown, the tool 10 includes a shaft 30 between the proximal end 14 and distal end 12. In this embodiment, the shaft 30 is curved so that proximal end 14 is raised above the distal end 12. This curvature allows clearance between the hand of the user gripping the handle 16 and the surface of the skin when the tool 10 is in use. Typically, the underside of the guide 20 rests against or is aligned with the surface of the skin, as indicated by dashed line. In this embodiment, the shaft 30 extends up toward the handle 16 at an angle θ with the surface of the skin. In some embodiments, the angle θ ranges from 0 to 90 degrees, more preferably from 15 to 45 degrees. Or, the shaft 30 extends up toward the handle 16 so that the handle starts at a distance h from the surface of the skin. In some embodiments, the distance h is approximately 3 inches. In other embodiments, the distance h ranges from 0 to 3 inches, or from 0 to 1.5 inches.

Figure 2A:
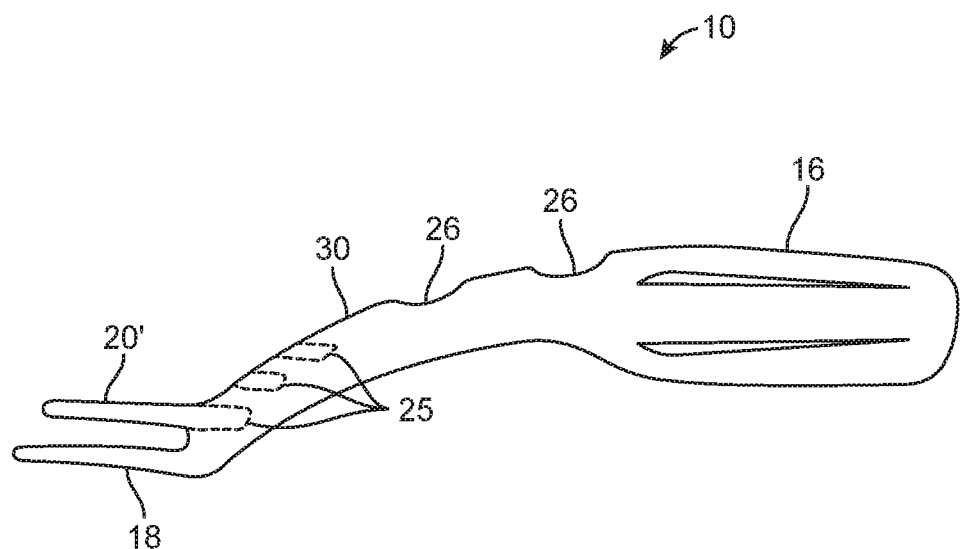
FIG. 2A illustrates a tool having a guide which is removable and repositionable along the shaft
Figure 2B:
FIGS. 2B-2C illustrate an example removable guide having a fixation mechanism comprising a double-sided ball detent.
Figure 2C:
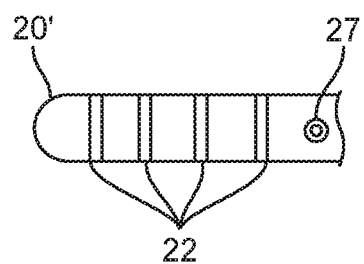

In some embodiments, the tool 10 has a guide 20 and tunneling member 18 that are a fixed distance apart. In other embodiments, the distance between the guide 20 and tunneling member 18 is adjustable. In either case, the distance between the guide 20 and tunneling member 18 are typically 0.1 to 3 cm apart, optionally 0.5 to 3 cm apart. FIG. 2A illustrates a tool 10 having a guide 20' which is removable and repositionable along the shaft 30. The shaft 30 includes one or more receptacles 25 for receiving the removable guide 20'. The receptacles 25 are disposed along the shaft 30 at various distances from the tunneling member 18. This positioning allows the user to adjust the depth beneath the skin surface at which the tunneling member 18 creates the tissue channel. Each removable guide 20' is held within the receptacle 25 with a fixation mechanism 27. FIGS. 2B-2C illustrate an example removable guide 20' having a fixation mechanism 27 comprising a double-sided ball detent. FIG. 2B is a side view of the guide 20' and FIG. 2C is a top view of the guide 20'. In this embodiment, each receptacle 25 includes a corresponding indent to receive the ball detent. This mating locks the guide 20' in place. It may be appreciated that in other embodiments, the distance between the guide 20 and tunneling member 18 can be adjusted by other mechanisms. For example, the guide 20 may slide up and down the shaft 30 by manipulation of a lever or knob on the tool 10.

Figure 3:
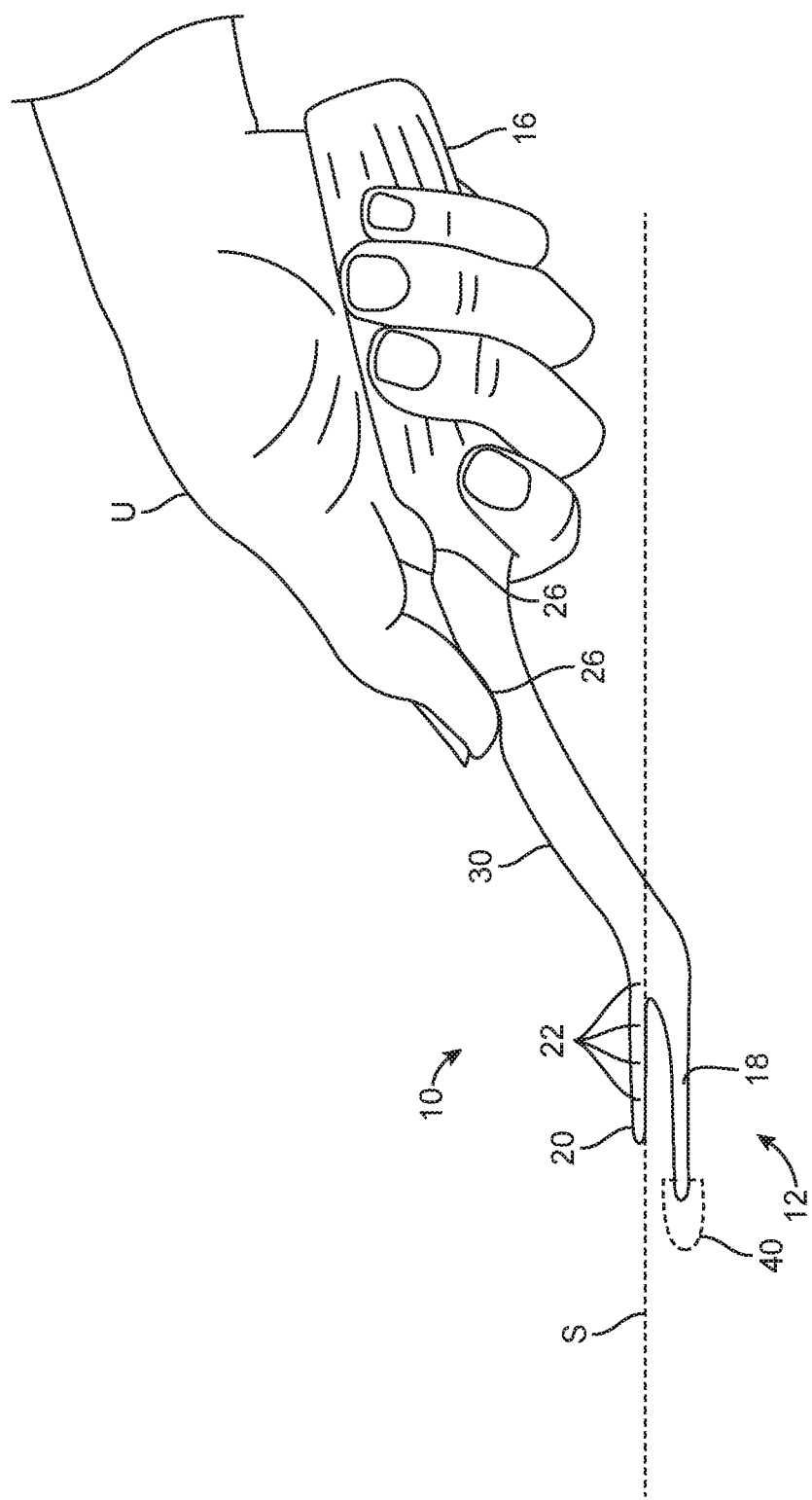
FIG. 3 illustrates the tunneling tool of FIG. 1A in use.

FIG. 3 illustrates the tunneling tool 10 of FIG. 1 in use. As shown, a user U grips the handle 16 to manipulate the tool 10. Here, the user U positions a thumb against an indent 26 for leverage. It may be appreciated that any suitable grip may be used, including positioning an index finger or other finger against one or more indents 26. The distal end 12 of the tool 10 is positioned so that the tunneling member 18 is advanced through a small incision in the skin S. The tool 10 is then advanced by manipulating the handle 16 so that the tunneling member 18 bluntly dissects the subcutaneous tissue creating a tissue channel while the guide 20 remains above the skin S, as shown. Typically, the tunneling member 18 is advanced until it reaches an implantation area 40. The implantation area 40 is the area within which a device or other implantable is desired to be positioned beneath the skin. Thus, the tunneling member 18 has created a tunnel from the incision point to the implantation area 40.

Figure 4:
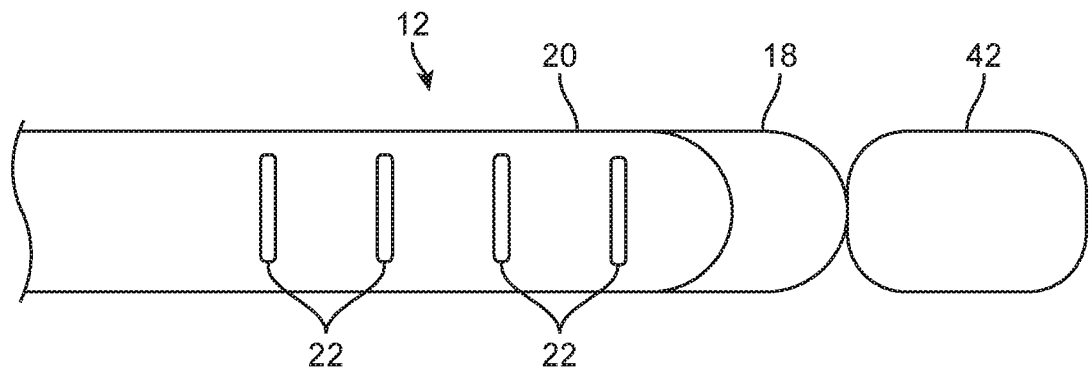
FIG. 4 schematically illustrates an embodiment of an example implantable which may be advanced through a tissue channel created by the tunneling tool.

The implantable can then be advanced to the implantation area 40. FIG. 4 schematically illustrates an embodiment of an example implantable 42 which may be advanced through the tissue channel. It may be appreciated that a variety of implantables 42 may be used, including but not limited to stimulators, antennas, infusion ports and pumps, pills, catheters, biological monitors (e.g., glucose, cardiac, blood pressure, etc.). Typically, the implantable 42 has external dimensions that are similar to some aspects of the tunneling member 18 so that the implantable 42 may be passed through the tissue channel created by the tunneling member 18. Preferably, the dimensions of the tunneling member 18 are chosen so as to create a very snug pocket around the implantable 42 when implanted. For example, in some instances the tunneling member 18 is undersized in comparison to the implantable 42 so as to allow the tissue channel to stretch slightly around the implantable 42. In some instances, the implantable 42 is pushed by the distal tip of the tunneling member 18, advancing the implantable 42 through the tissue channel to the implantation area 40, as indicated by FIG. 4.

Figure 5A:
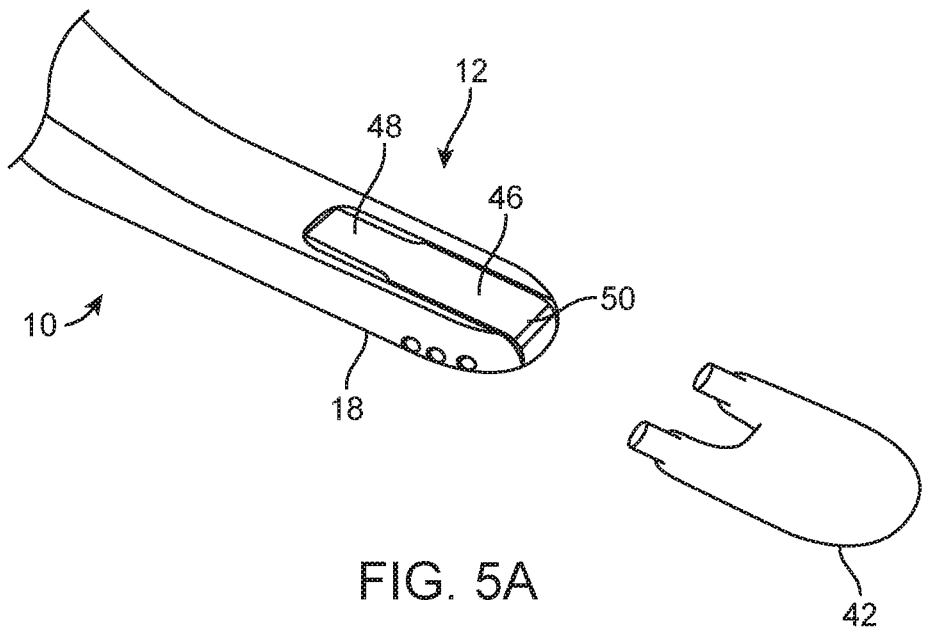
FIGS. 5A-5B illustrate an implantable attachable to the tunneling tool by a mount.
Figure 5B:
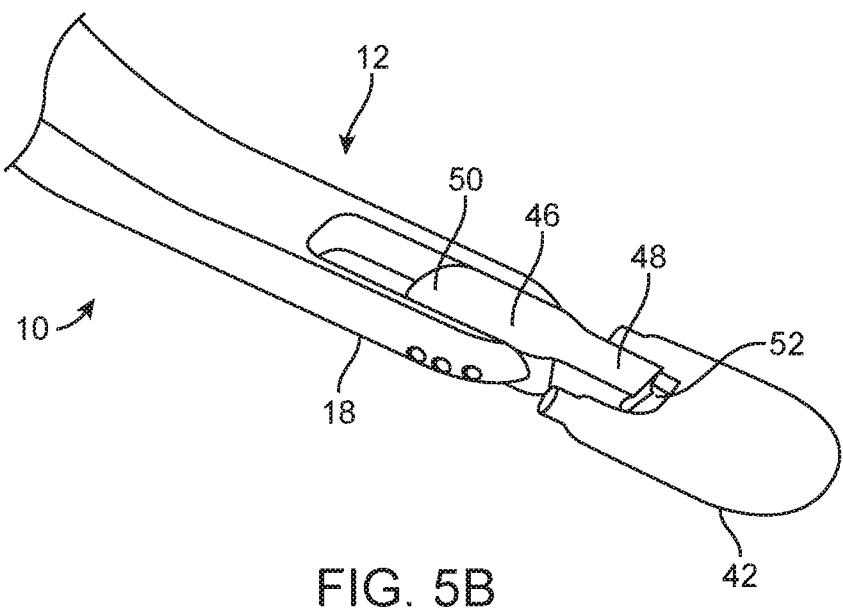

In other embodiments, the implantable 42 is attachable to the tunneling tool 10, as illustrated in FIGS. 5A-5B. In this embodiment, the distal end 12 of the tunneling tool 10 includes a mount 46 for mounting an implantable 42 thereon during delivery. In particular, the mount 46 includes a mounting end 48 which is configured to mate with the implantable 42. FIG. 5A illustrates an embodiment of a distal end 12 of a tunneling tool 10 (with the guide removed for clarity), wherein a mount 46 is disposed within the tunneling member 18 and arranged in a stored position. In the stored position, the mounting end 48 is stored within the tunneling member 18 and an opposing end 50 faces outward, creating a blunt, atraumatic tip with the tunneling member 18. The tool 10 is used in this arrangement to create the tissue channel. The tool 10 is then removed from the patient, and the mount 46 is manipulated to a receiving position wherein it is available to receive the implantable 42. In this embodiment, as illustrated in FIG. 5B, the mount 46 is rotatable so that the mounting end 48 is rotated from within the tunneling member 18 to a position wherein the end 48 extends outward, beyond the distal tip of the tunneling member 18, when in the receiving position. In this embodiment, the mounting end 48 includes a recess 52 which mates with a contour of the implantable 42. This allows the tool 10 to be removably attached to the implantable 42 during delivery. Thus, once the tissue channel has been created, the tool 10 with the mounted implantable 42 is inserted into the tissue channel and advanced until the implantable 42 is desirably positioned within the implantation area 40. The tool 10 is then withdrawn (e.g. after releasing tool 10 from implantable 42), leaving the implantable 42 behind.

Figure 6:
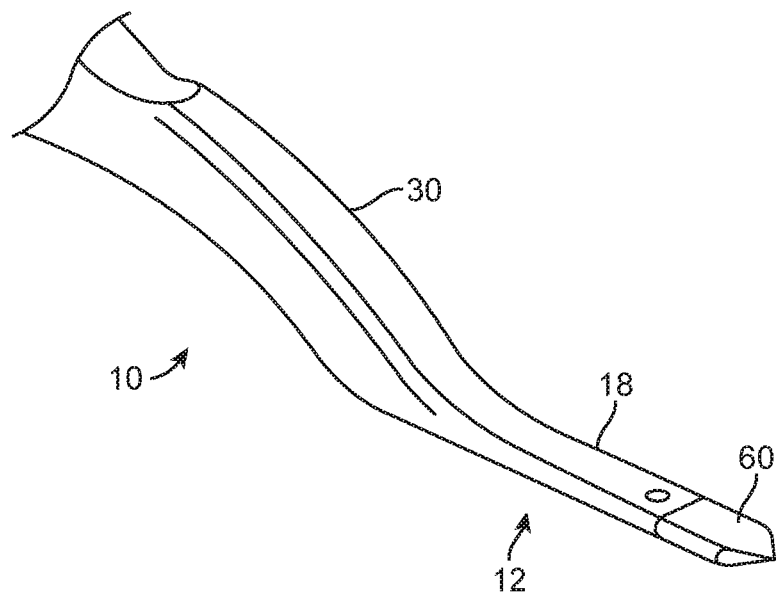
FIG. 6 illustrates a tunneling member having a cutting tip.
Figure 7:
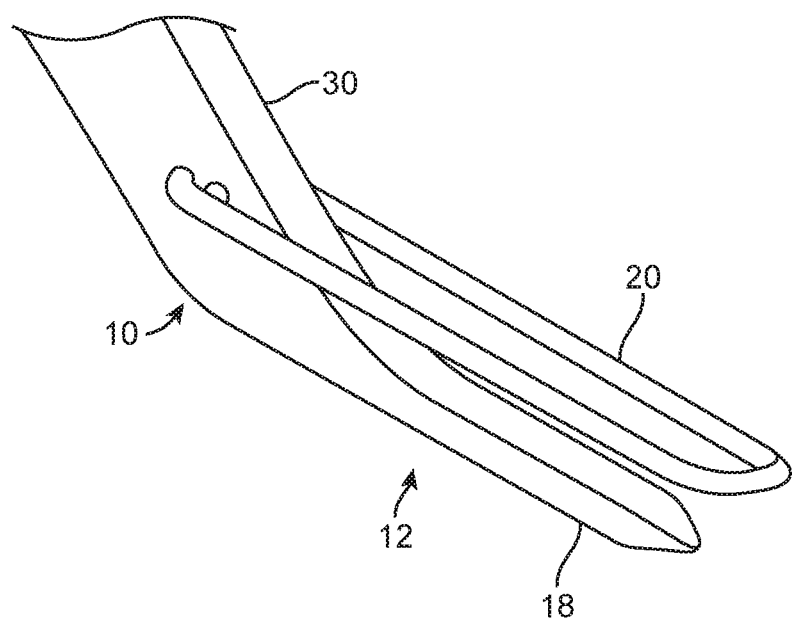
FIG. 7 illustrates a tunneling member having an open window guide and a tunneling member with a tapered design.

It may be appreciated that the tunneling member 18 may have a variety of distal tips. When blunt dissecting is desired, a round, blunt tip design may be used, as illustrated in FIG. 1A. Alternatively, when cutting, a tunneling member 18 having a cutting tip 60 may be used, an embodiment of which is illustrated in FIG. 6. In this embodiment, the distal most tip of the tunneling member 18 includes a cutting tip 60 or blade configured to cut tissue while creating the tissue channel. The cutting tip 60 may be integral with the tunneling member 18 or removable and replaceable. In other embodiments, the distal tip of the tunneling member 18 has a tapered design, as illustrated in FIG. 7. Such a tapered design may be used when passing through tissue that is too delicate for cutting yet too dense for blunt dissection.

It may be appreciated that the guide 20 may also have a variety of forms. FIG. 7 illustrates a guide 20 having an open window. Such an open window allows the user to see the surface of the skin while visualizing the perimeter of the tunneling member 18 under the skin. This may be useful when avoiding particular areas of the skin or when utilizing features of the skin to steer or anticipate changes in resistance when creating the tissue channel.

Figure 8A:
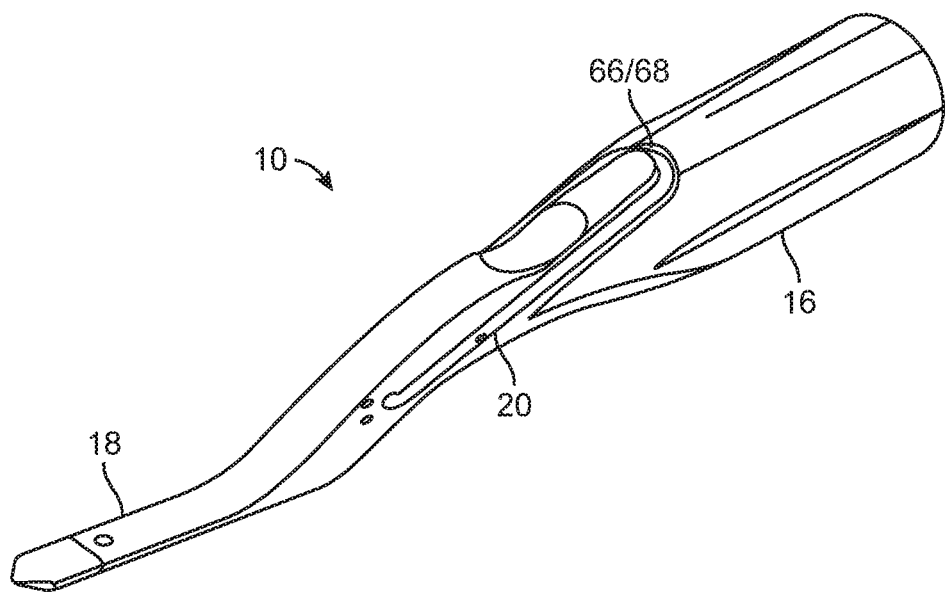
FIGS. 8A-8B illustrate manipulation of an open window guide for optional usage.
Figure 8B:
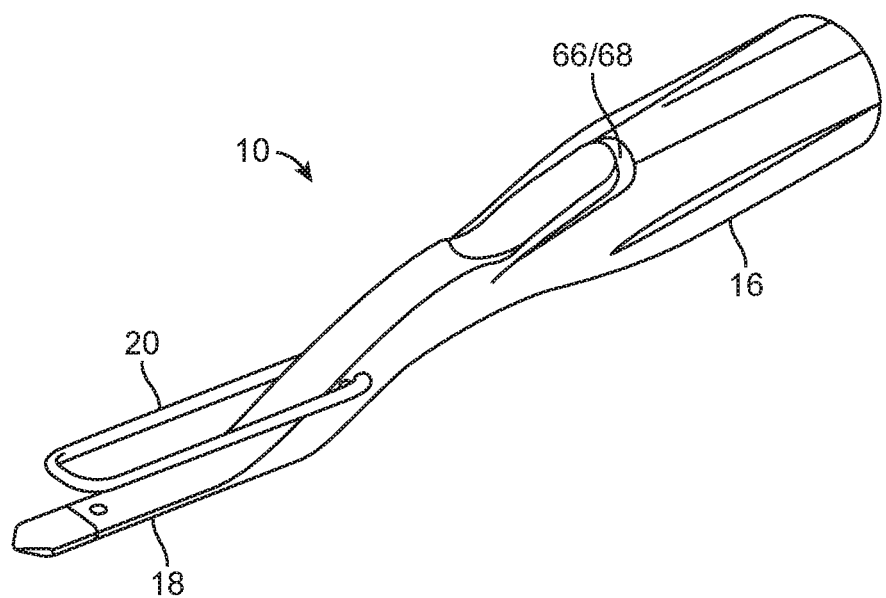

The open window guide 20 also lends itself to easy storage, as illustrated in an embodiment depicted in FIGS. 8A-8B. In this embodiment, the tunneling tool 10 includes a storage receptacle 66 for receiving and storing the guide 20 when not in use. In particular, the receptacle 66 comprises a groove 68 or indent in the handle 16 which receives portions of the open window guide 20. FIG. 8A illustrates the guide 20 rotated upwards, away from the tunneling member 18, and mated with the receptacle 66. Such mating provides a smooth, ergonomic contour to the handle 16 which does not interfere with the grip of the user. The guide 20 may then be removed from the receptacle 66 and rotated downward so that it is desirably aligned with the tunneling member 18.

It may be appreciated that in addition to using the tunneling tool 10 to create a tissue channel, the tunneling tool 10 may also be used to create a subcutaneous pocket (e.g. into which a non-elongate device is to be implanted). Once the tunneling member 18 is positioned into the subcutaneous tissue, the tunneling member 18 may be manipulated to create a pocket therein which is larger than the tissue channel. For example, the tool 10 may be rotated around an axis perpendicular to the skin surface so as to swing the tunneling member 18 through a radius. Similarly, the tool 10 may be moved laterally to create a wider tunnel. Further, the tunneling member 18 may have various shaped tips to create different types of tunnels or pockets (e.g. tapered tips or bulbous tips).

Figure 40A:
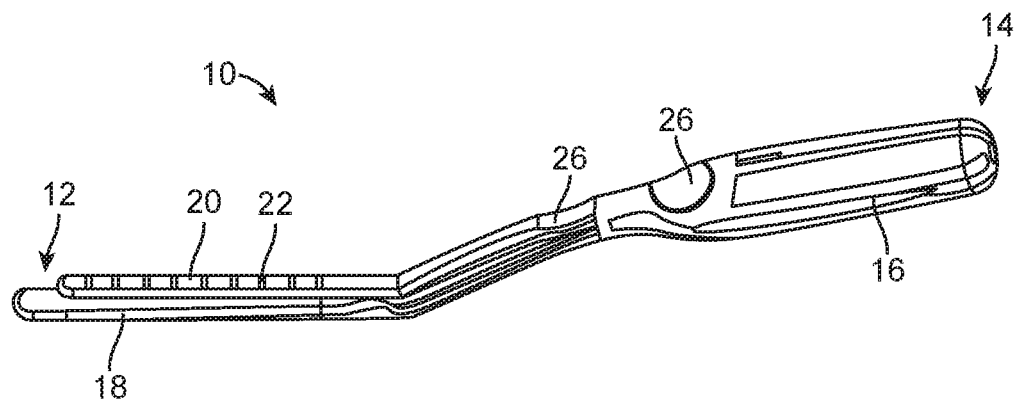
FIGS. 40A-C are perspective, top, and side views, respectively, of a tunneling tool configured for tunneling into subcutaneous tissue structured within the body.
Figure 40B:
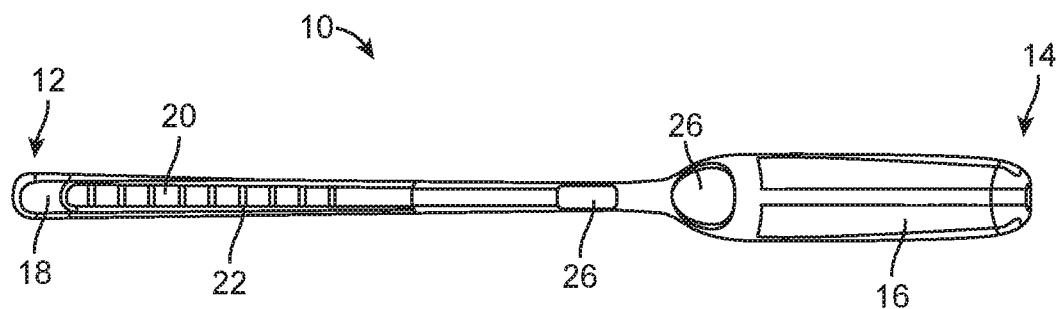
Figure 40C:
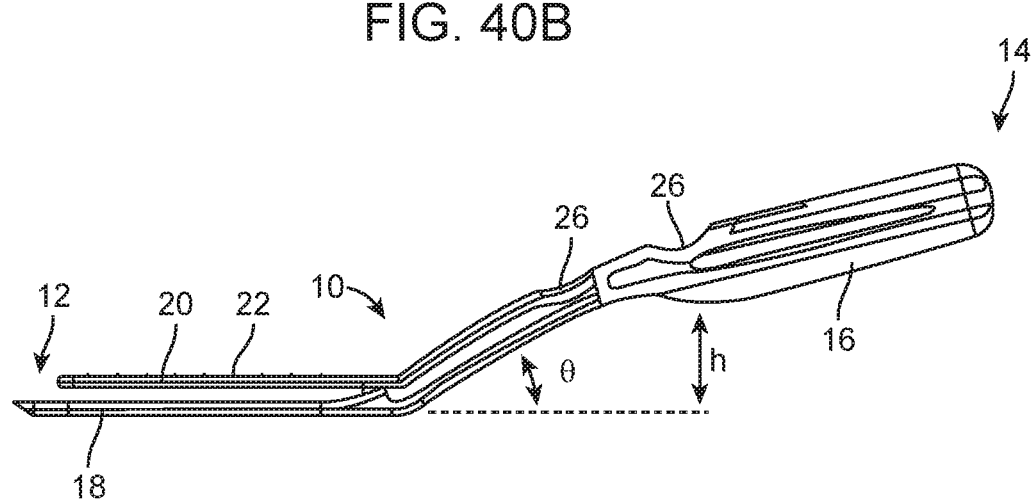

FIGS. 40A-C are perspective, top, and side views, respectively, of an embodiment of a tunneling tool wherein the tunneling tool is configured for tunneling into subcutaneous tissue structured within the body. The tunneling tool 10 has a distal end 12 with a tunneling member 18 and a guide 20, and a proximal end 14. Tunneling tool 10 can be of similar construction and arrangement to tool 10 described hereabove in reference to FIGS. 1A and 1B. In the embodiment shown in FIGS. 40A-C, tunneling member 18 and guide 20 each comprise an enlarged distal end, such as the outwardly tapered distal end shown, and/or a bulbous distal end. Guide 20 can comprise a length that is less than the length of tunneling member 18, and guide 20 can comprise a width that is less than the width of tunneling member 18.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Anchors

The anchors of the present invention are configured to lock onto an elongate device, such as a catheter, lead or other device implantable within the body. The anchor is then used to attach the elongate device to the surrounding tissue, thereby anchoring the device, either by suturing of features on the anchor or by the anchor itself. Typically, such elongate devices have a soft durometer and are easily kinked or damaged by direct suturing. Therefore, these anchors provide the ability to hold the device with minimal to no impingement or damage to the device and provide a platform upon which to robustly secure the anchor to its surroundings. For ease of description, the elongate device is referred to herein as a lead, however the invention is not so limited.

Figure 9:
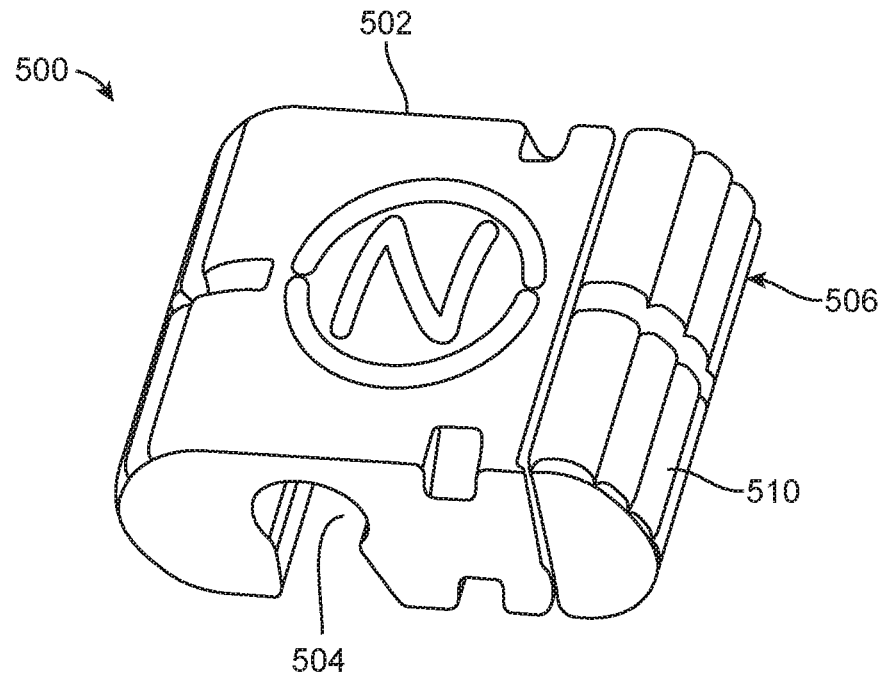
FIG. 9 is a perspective illustration of an embodiment of an anchor comprised of two components which mate to lock onto an elongate device, such as a lead.
Figure 10:
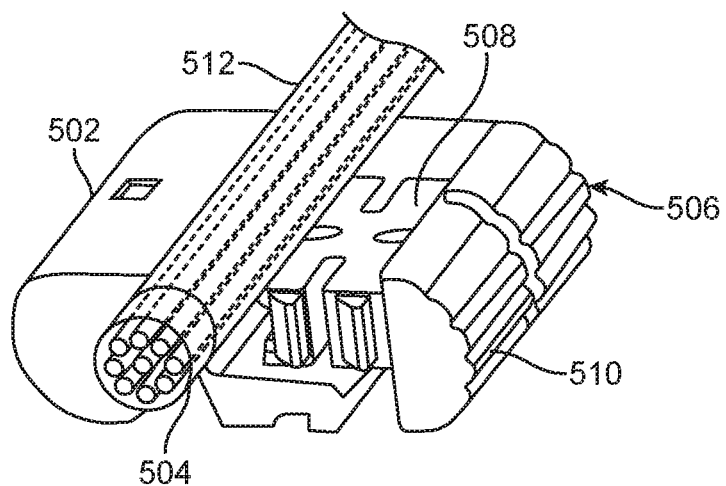
FIG. 10 illustrates a protrusion insertable into a base which is pressed, by applying force to the grip, into the base so that it reaches the passageway and applies mechanical and frictional retention to a lead positioned therein.

FIG. 9 is a perspective illustration of an embodiment of an anchor 500 which locks onto an elongate device, such as a lead. In this embodiment, the anchor 500 comprises two components which mate together to lock onto the lead. A first component comprises a base 502 having a lumen, passageway 504, for positioning a lead therethrough or therein. A second component comprises a locking member 506 which mates with the base 502. In this embodiment, the locking member 506 comprises a protrusion 508 and a grip 510. Referring to FIG. 10, the protrusion 508 is insertable into the base 502 and can be pressed, by applying force to the grip 510, into the base 502 so that it reaches the passageway 504 and mechanically compresses the lead 512 positioned therein. Such compression and frictional forces lock the anchor 500 onto the lead 512.

Figure 11:
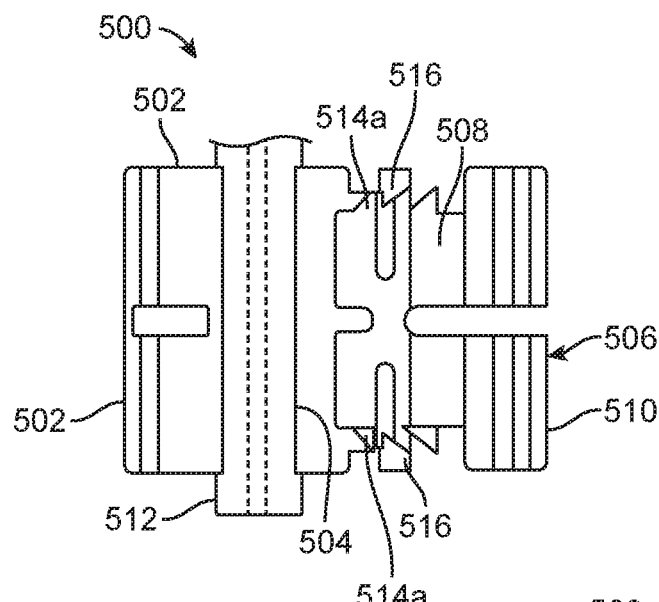
FIGS. 11-12 provide top view illustrations of the anchor of FIG. 10 in open and closed configurations.
Figure 12:
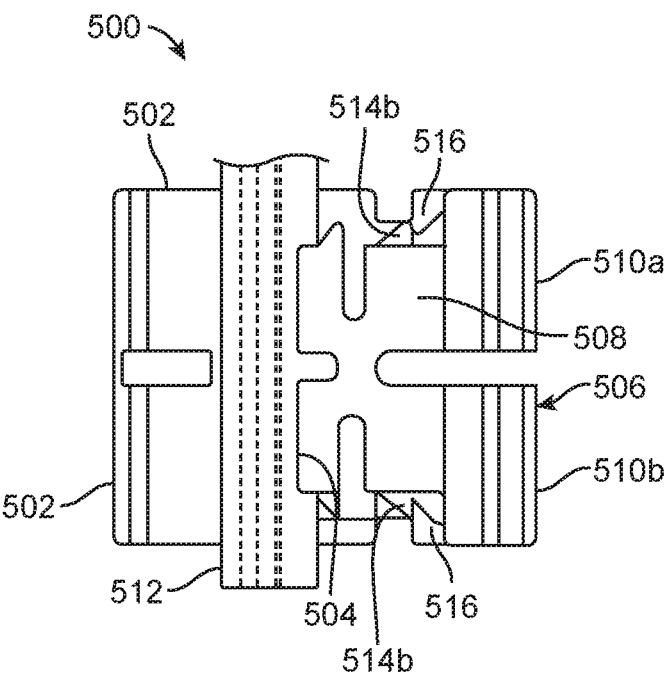

FIGS. 11-12 provide top view illustrations of the anchor 500 of FIG. 10 in open and closed configurations. FIG. 11 illustrates the anchor 500 in an open configuration wherein the anchor 500 is not locked to the lead 512. In this configuration, the locking member 506 is in a first position wherein the protrusion 508 is engaged with the base 502 to ensure integrity of the anchor 500 but the protrusion 508 is not contacting the lead 512. In this embodiment, the protrusion 508 includes one or more teeth 514a which engage with a flange, hole or lip 516 within the base 502 so that the locking member 506 cannot be removed. In this open configuration, the anchor 500 can be moved along the lead 512, either by sliding along the length of the lead 512 or by disengaging and re-engaging with the lead 512 at any position along the lead body. Once the anchor 500 is desirably positioned along the lead 512, the anchor 500 can be moved to a closed configuration, wherein the anchor 500 is fixed to the lead 512. FIG. 12 illustrates the anchor 500 in a closed configuration wherein the locking member 506 is pressed into the base 502 so that the protrusion 508 contacts the lead 512 by a side approach to the passageway 504. In this embodiment, the protrusion 508 includes one or more teeth 514*b* which engage with the lips 516 within the base 502 to hold the locking member 506 in this closed configuration. Thus, the teeth 514*a*, 514*b* are spaced apart to allow the locking member 506 to transition from the open configuration to the closed configuration. Likewise, the lips 516 are positioned so as to hold the locking member 506 at a fixed clamping position, a position that applies a desired level of force to the lead 512 so that the lead 512 is held in place without impingement or damage. The distance between the front of the protrusion 508 and the teeth 514*b* may be modulated to create more or less clamping force on the lead. This distance is known within the overall dimensional proportions of the assembly and can be used to predictively restrict overclamping of the lead.

If desired, the anchor 500 can then be disengaged from the lead 512 by transitioning back to the open configuration. This transition is achieved by disengaging the teeth 514*b* from the lips 516. In this embodiment, such disengagement is achieved by squeezing a first portion of the grip 510*a* and a second portion of the grip 510*b* together. Such squeezing draws each of the teeth 514*b* inward, away from the lips 516, thereby allowing the teeth 514*b* to disengage and pass by the lips 516, so that the anchor 500 is again in the open configuration. The specific geometry of the protrusion 508 and the relief cuts therein prevent a user from completely disengaging the locking member 506 from the base 502, therefore maintaining the integrity of the assembly over multiple use cycles. The anchor 500 can be switched between the open configuration and the closed configuration as many times as desired for repositioning.

Figure 13:
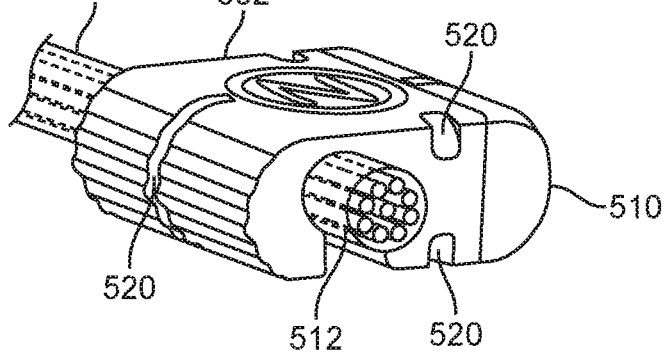
FIG. 13 illustrates the anchor of FIG. 10 fixed to a lead.

Once, the anchor 500 is desirably fixed to the lead 512, as illustrated in FIG. 13, the anchor 500 is then attached to the surrounding tissue. In this embodiment, the anchor 500 includes one or more suture retention detents 520 to receive suture. Thus, suture can be wrapped around the anchor 500 without slipping. It may be appreciated that in other embodiments, the anchor 500 includes one or more through-holes for receiving suture. And, in other embodiments, the anchor 500 has tissue grabbing jaws or other tissue engagement elements which take advantage of the relative movement between the base 502 and the locking member 506, such as to eliminate the need for suturing.

It may be appreciated that the passageway 504 may alternatively be fully captured by the base 502. In such instances, the anchor 500 is loaded onto the lead 512 from one end of the lead 512 and is moved along the lead length to the desired position.

It may be further appreciated that the locking member 506 may alternatively utilize other mechanisms for transitioning between the open configuration and the closed configuration and maintaining the closed configuration. For example, the locking member 506 may be spring loaded within the base 502 so as to bias the locking member 506 toward a particular configuration. Alternatively, the locking member 506 may include a rack and pinion mechanism to transition between the configurations and maintain the closed configuration.

It may also be appreciated that the surfaces of the anchor 500 which contact the lead 512 may be modified to increase retention force. These surfaces may include portions of the passageway 504 and/or portions of the protrusion 508 which contact the lead 512. Such surfaces may be textured, have a higher coefficient of friction, such as a soft durometer silicone, and/or include gripping features such as barbs. These gripping features may be unidirectional and/or bidirectional gripping elements.

It may also be appreciated that in some embodiments, the anchor 500 is deployed via an injection tool. Such deployment may be desired to minimize the size of the incision used to manipulate an anchor. The anchor 500 may be delivered along the lead body such that the incision need only allow clearance for the anchor. In some embodiments, the injection tool also actuates the transition to the closed configuration upon deployment.

Figure 14:
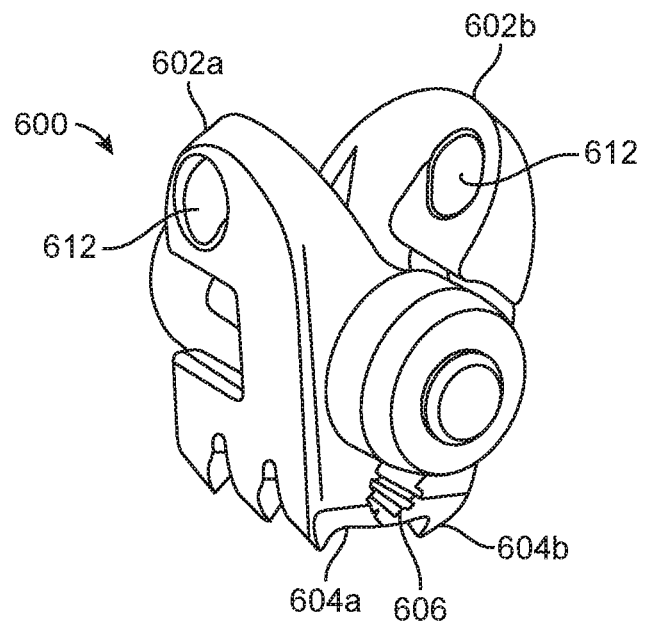
FIG. 14 is a perspective illustration of an embodiment of an anchor comprising a first component having a first lever arm and a first jaw, and a second component comprised of a second lever arm and a second jaw.
Figure 15:
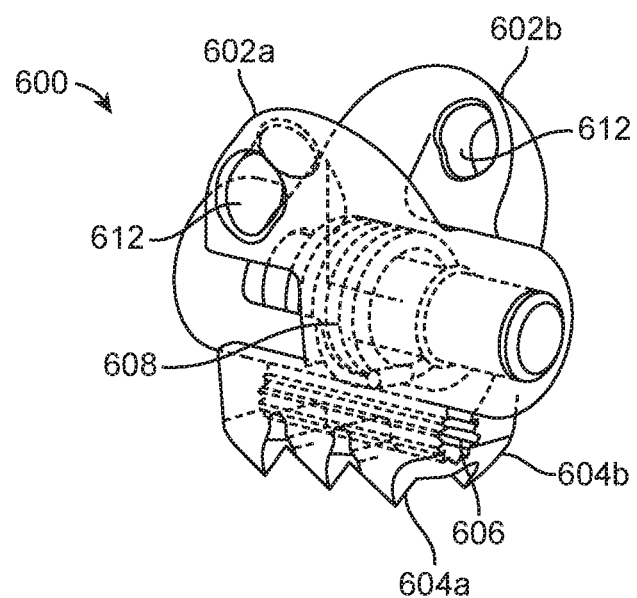
FIG. 15 provides an illustration showing an internal torsion spring housed within the anchor of FIG. 14.

FIG. 14 is a perspective illustration of an embodiment of an anchor 600 which locks onto an elongate device, such as a lead. In this embodiment, the anchor 600 is comprised of two components which mate together to lock onto the lead. A first component is comprised of a first lever arm 602*a* and a first jaw 604*a* that may be integrated into a single component (as depicted) or are the result of an assembly of individual parts. The second component is comprised of a second lever arm 602*b* and a second jaw 604*b*. The components mate together so that the first and second lever arms 602*a*, 602*b* are aligned and the first and second jaws 604*a*, 604*b* are aligned to form a lumen, passageway 606, for receiving the lead. FIG. 15 provides an illustration showing an internal torsion spring 608 housed within the anchor 600. The spring 608 biases the lever arms 602*a*, 602*b* away from each other and the jaws 604*a*, 604*b* toward each other. Thus, the spring 608 biases the anchor 600 toward a closed configuration. The selection of an appropriate torsion spring with particular material and geometric properties influences the degree of bias, i.e., the amount of force with which the jaws 604*a* and 604*b* are closed towards one another, such as when engaging lead 512.

Figure 16:
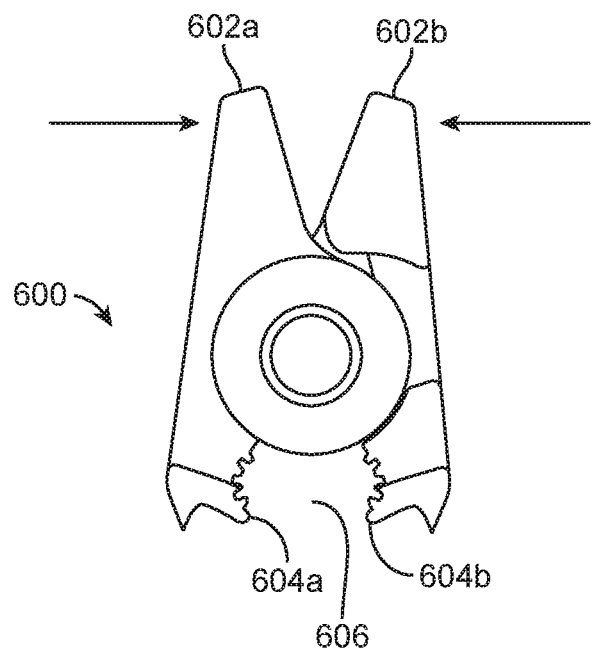
FIG. 16 illustrates the anchor of FIG. 14 in an open configuration.
Figure 17A:
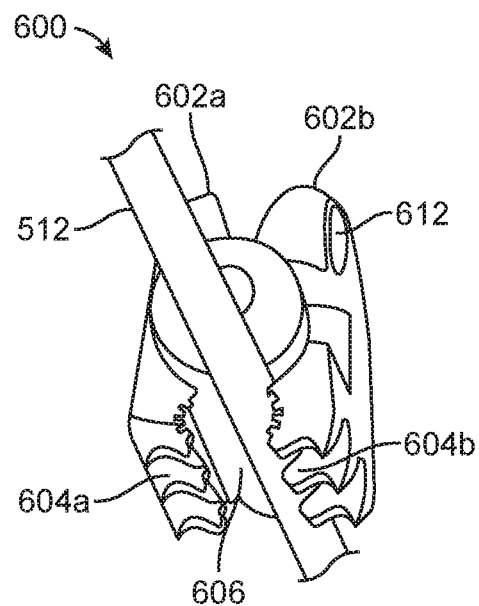
FIG. 17A illustrates the anchor of FIG. 14 in the open configuration straddling the lead, wherein the lead is disposed within the passageway.
Figure 17B:
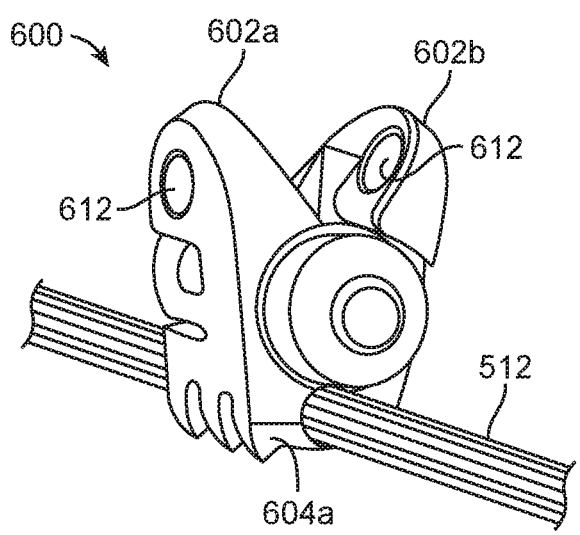
FIG. 17B illustrates the anchor of FIG. 14 transitioned to a closed configuration to fix the anchor to the lead.

The anchor 600 is transitioned from the closed configuration to an open configuration by moving the lever arms 602*a*, 602*b* toward each other, as illustrated in FIG. 16 and indicated by arrows. Moving the lever arms 602*a*, 602*b* toward each other correspondingly moves the first and second jaws 604*a*, 604*b* away from each other. This enlarges the passageway 606. In the open configuration, the anchor 600 can be positioned along a lead at any desired location. FIG. 17A illustrates the anchor 600 in the open configuration straddling the lead 512, wherein the lead 512 is disposed within the passageway 606. Since the passageway 606 is enlarged in the open configuration, the anchor 600 can be moved along the lead 512 as desired without friction. Once desirably positioned along the lead 512, the anchor 600 can be transitioned to a closed configuration to fix the anchor 600 to the lead 512, as illustrated in FIG. 17B. This is achieved by releasing the lever arms 602*a*, 602*b* so that torsion spring 608 moves the lever arms 602*a*, 602*b* apart and draws the jaws 604*a*, 604*b* together, clamping the jaws 604*a*, 604*b* onto the lead 512. The lead 512 is held in place by mechanical compression and friction between the jaws 604*a*, 604*b*. The clamping force provided by the torsion spring 608 and/or the distance between the jaws 604*a*, 604*b* can be chosen so as to ensure that the lead 512 is held in place without impingement or damage. This construction reduces the potential for overclamping (e.g. overclamping which may damage lead 512). In some embodiments, the clamping force may be limited by the purposeful interference of features within the geometry of the lever arms 602*a*, 602*b*. It may be appreciated that the surfaces of the anchor 600 which contact the lead 512 may be modified to increase retention force. These surfaces include portions of the passageway 606 which contact the lead 512. Such surfaces may be textured, have a higher coefficient of friction, such as a soft durometer silicone, and/or include gripping features such as barbs. These gripping features may be unidirectional and/or bidirectional gripping elements.

The anchor 600 can be repositioned by pinching the opposing lever arms 602*a*, 602*b* to transition back to the open configuration, repositioning the anchor 600 along the lead 512, and then releasing the lever arms 602*a*, 602*b* to fix the anchor 600 at the new location. Thus, the anchor 600 can be attached and reattached to the lead 512 without loading from an end of the lead 512.

Once desirably positioned, the anchor 600 can be sutured to the surrounding tissue. In this embodiment, each lever arm 602*a*, 602*b* includes a suture eyelet 612 for passing suture therethrough and fixing the anchor 600 to the tissue. In other embodiments, the anchor 600 has tissue grabbing jaws which can eliminate the need for suturing.

Figure 18A:
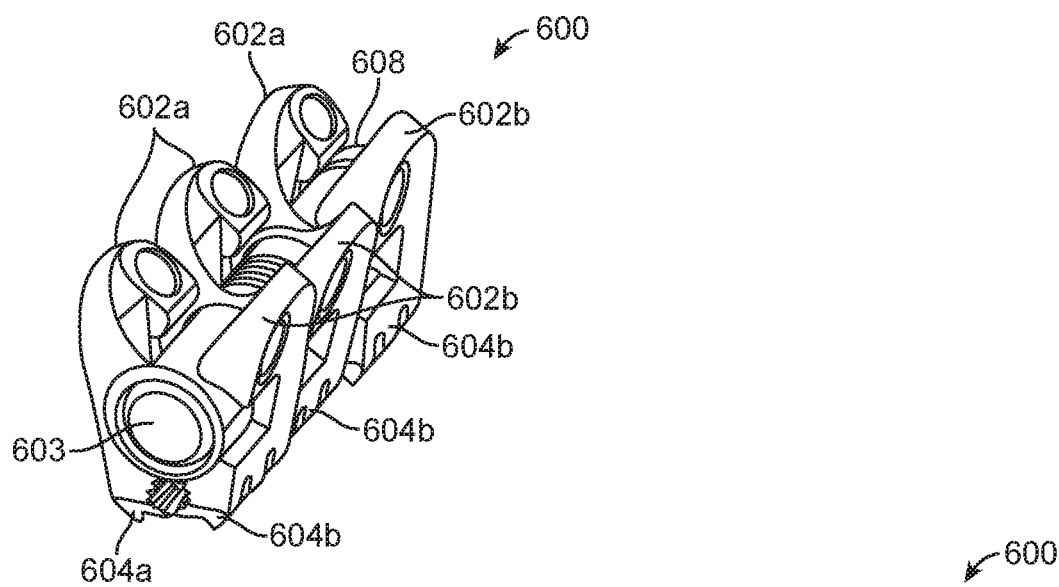
FIGS. 18A-18C illustrate an embodiment of an anchor having more than one set of lever arms and corresponding jaws.
Figure 18B:
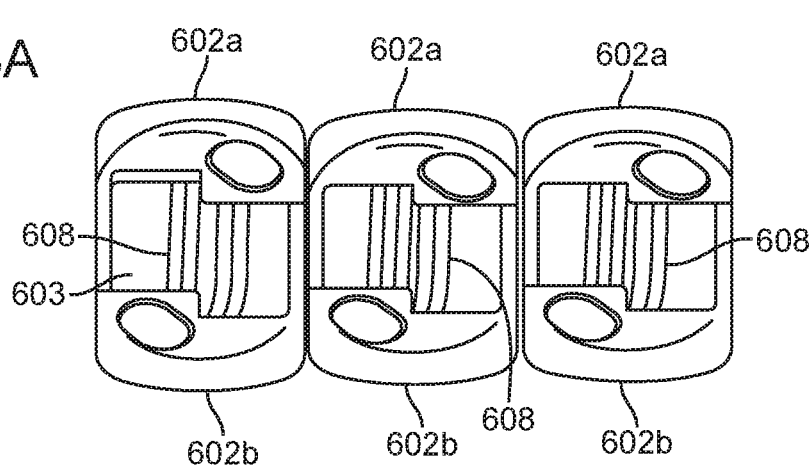
Figure 18C:
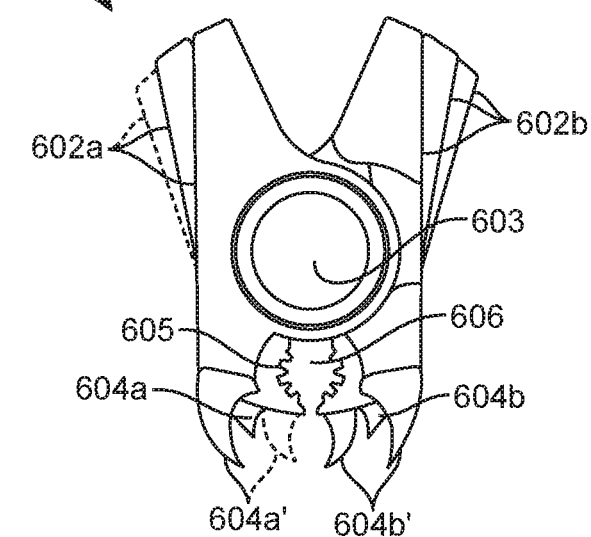

In some embodiments, the anchor 600 has more than one set of lever arms 602*a*, 602*b* and corresponding jaws 604*a*, 604*b*, as illustrated in FIGS. 18A-18C. This multiple arm configuration allows some sets to be utilized for holding the lead 512 and other sets to be utilized for grasping the surrounding tissue to hold the anchor 600 in place. FIG. 18A provides a perspective view of an anchor 600 having three sets of lever arms 602*a*, 602*b* and corresponding jaws 604*a*, 604*b*. The sets are aligned in a series utilizing a common pin 603 around which three corresponding torsion springs 608 are disposed. FIG. 18B provides a top view of the anchor 600 of FIG. 18A illustrating the springs 608. The springs 608 may have the same strength or differing strengths. In some embodiments, the springs 608 corresponding to jaws 604*a*, 604*b* configured for grasping surrounding tissue have a stronger spring force than the springs 608 corresponding to jaws 604*a*, 604*b* configured for grasping the lead 512. FIG. 18C provides an end view illustration of an embodiment having longer tissue grasping jaws 604*a*', 604*b*' straddling jaws 604*a*, 604*b* primarily intended for grasping the lead. The jaws 604*a*, 604*b* intended to grasp the lead have a contact surface 605 configured for holding the lead within the passageway 606. The lever arms 602*a*, 602*b* may be moved independently, or actuation of a single pair of lever arms 602*a*, 602*b* may actuate the entire series of lever arms 602*a*, 602*b*, thereby opening all of the jaws 604*a*, 604*b* in unison. It may be appreciated that any combination of independent arms and linked arms may occur in various embodiments.

Figure 19:
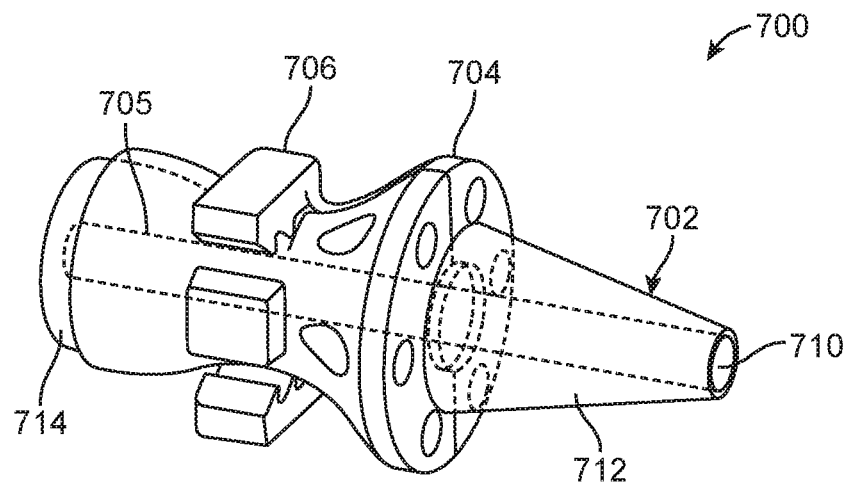
FIGS. 19, 20, 21, 22, 23 illustrate an embodiment of an anchor comprised of a sleeve, an anchor body and a locking mechanism, wherein the anchor body has two portions which are held together by the locking mechanism.

FIG. 19 is a perspective illustration of another embodiment of an anchor 700 which locks onto an elongate device, such as a lead. In this embodiment, the anchor 700 is comprised of a sleeve 702, an anchor body 704 and a locking mechanism 706. The anchor body 704 is comprised of a first body portion 704*a* and a second body portion 704*b* which mate together forming a body lumen 705 therebetween. The body lumen 705 is configured to receive the sleeve 702. The locking mechanism 706 is positionable at least partially around the anchor body 704 so as to hold the first body portion 704*a* and a second body portion 704*b* in the mated position.

Figure 20:
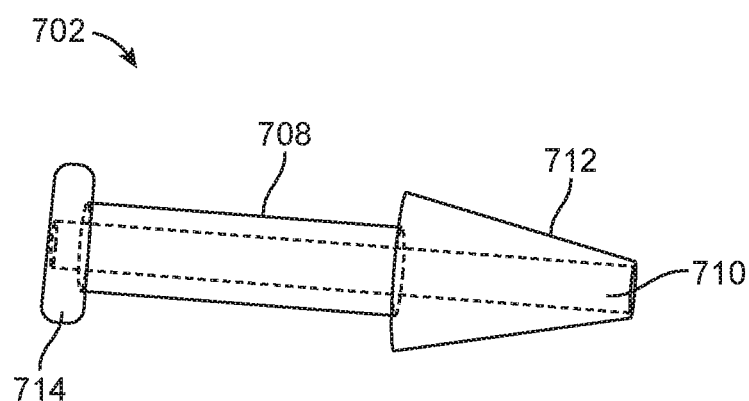

The sleeve 702 is typically comprised of a soft durometer material, such as a silicone material. In this embodiment, the sleeve 702, illustrated in FIG. 20, comprises an elongate shaft 708 having a lumen 710 therethrough. The shaft 708 is sized and configured to fit within the body lumen 705 of the anchor body 704. The lumen 710 is sized and configured to receive the lead. In this embodiment, the shaft 708 has a tapered tip 712 to create a transition and strain relief for the lead as it exits the anchor 700 and to create a transition through tissue layers. In this embodiment, the sleeve 702 also includes a backstop 714. The sleeve 702 is shaped so that the anchor body 704 is held between the tapered tip 712 and the backstop 714 and does not slip out from the anchor body 704.

Figure 21:
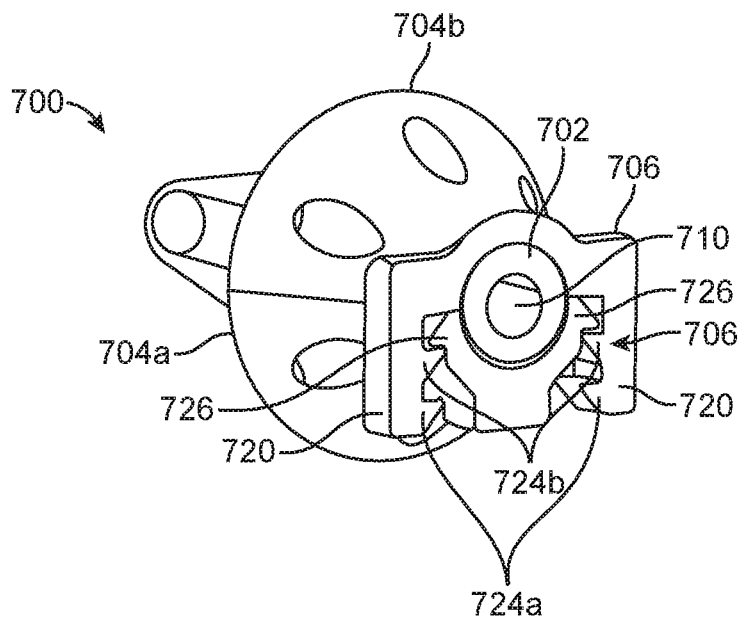
Figure 22:
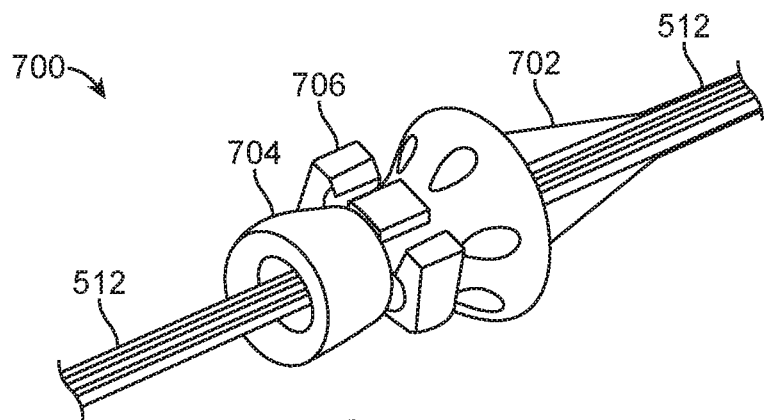

The anchor 700 is transitionable between an open configuration and a closed configuration by manipulation of the locking mechanism 706. FIG. 21 provides a cross-sectional view of the anchor 700 and locking mechanism 706. In this embodiment, the locking mechanism 706 comprises a snap closure mechanism including at least one arm 720 which extends around the anchor body 704. The arm 720 includes a pair of teeth 724*a*, 724*b* which individually engage a lip 726 on the anchor body 704. In the open configuration, one of the teeth 724*a* engages to the lip 726, allowing movement between the first body portion 704*a* and the second body portion 704*b*. In this configuration, the lead is insertable into the lumen 710 of the sleeve 702 and can move freely therein. Thus, the anchor body 704 can be moved along the lead to any desired location. Once the anchor body 704 is desirably positioned, the anchor 700 can be transitioned to the closed configuration. This transition is achieved by moving the arm 720 so that the other of the teeth 724*b* engages the lip 726 on the anchor body 704. This engagement tightens the mechanism 706 against the anchor body 704 and presses the first body portion 704*a* and the second body portion 704*b* together. Pressing of the body portions 704*a*, 704*b* together engages the lumen 710 with the lead, fixing the anchor 700 to the lead. The features of the locking mechanism 706, such as the distance between the teeth 724*a*, 724*b*, can be chosen so as to ensure that the lead is held in place without significant impingement or damage, reducing the potential for overclamping. It may be appreciated that the locking mechanism 706 may take other forms, such as a strap. FIG. 22 illustrates a lead 512 so positioned within the anchor 700.

Figure 23:
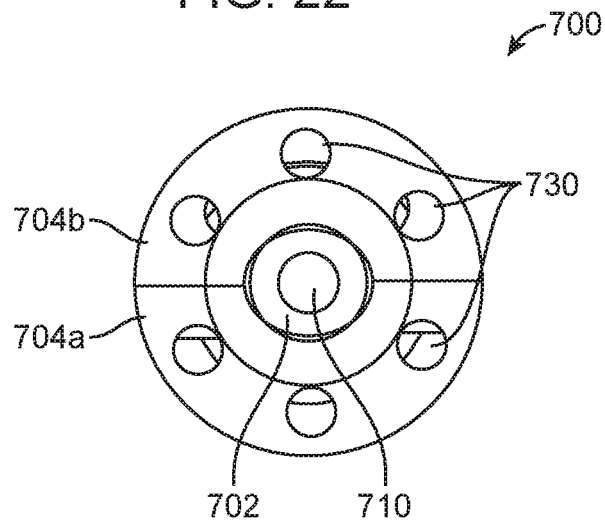

Once desirably positioned, the anchor 700 can be sutured to the surrounding tissue. In some embodiments, the anchor body 704 includes integrated suture eyelets 730, as illustrated in FIG. 23. Suture can be passed through each eyelet 730 for fixing the anchor 700 to the tissue. In this embodiment, the anchor body 704 also has a narrow waist which allows for suture retention.

It may be appreciated that the surfaces of the sleeve 702 which contact the lead 512 may be modified to increase retention force. These surfaces typically include portions of the lumen 710. Such surfaces may be textured, have a higher coefficient of friction, such as a softer durometer silicone, and/or include gripping features such as barbs. These gripping features may be unidirectional and/or bidirectional gripping elements. Overall, a soft durometer of the sleeve 702 distributes forces evenly along the lead 512, reducing potential for damage. Likewise, a soft durometer sleeve allows for easy customization of an associated coefficient of friction.

Figure 24:
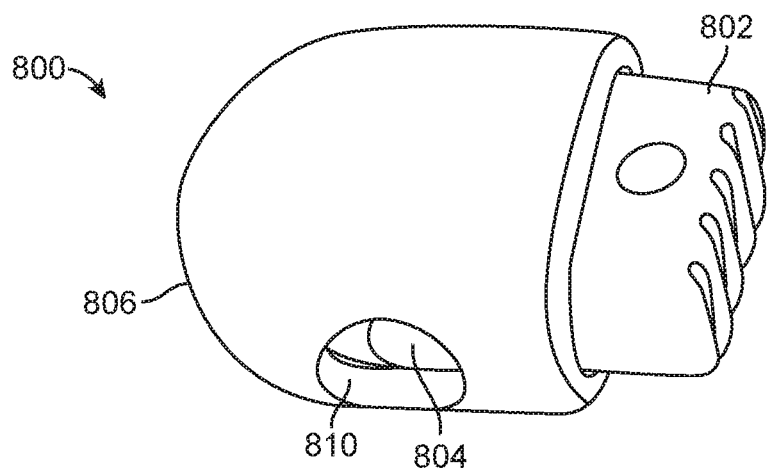
FIGS. 24, 25, 26 27, 28 illustrate an embodiment of an anchor comprised of a base having a passageway for positioning a lead therethrough or therein and a cover which extends at least partially over the base having at least two through holes, wherein the passageway and through holes are alignable for passage of a lead therethrough.
Figure 25:
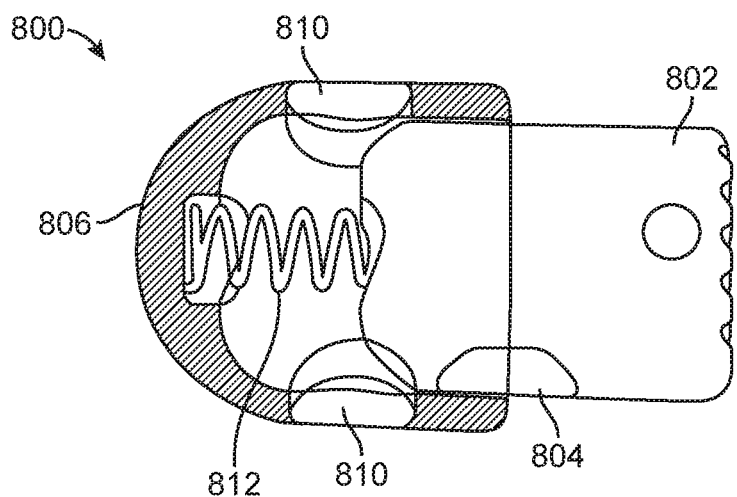
Figure 26:
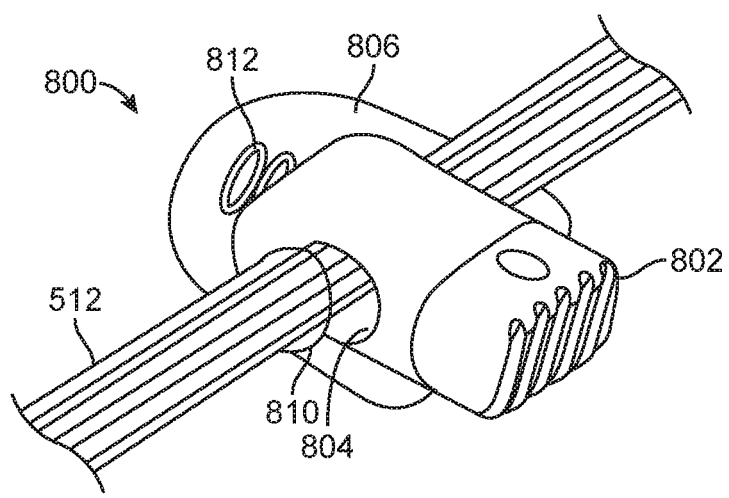

FIG. 24 is a perspective illustration of an embodiment of an anchor 800 which locks onto an elongate device, such as a lead. In this embodiment, the anchor 800 is comprised of two components which translate (e.g. slide) in relation to each other to lock the anchor 800 onto the lead. A first component comprises a base 802 having a lumen, passageway 804, for positioning a lead therethrough or therein. A second component comprises a cover 806 which extends at least partially over the base 802. In this embodiment, the cover 806 includes at least two through holes 810 which are alignable with the passageway 804, as shown. FIG. 25 illustrates the anchor 800 of FIG. 24 with a transparent view. As shown, the anchor 800 includes a spring 812 which biases the base 802 and the cover 806 apart, particularly biasing the through holes 810 and the passageway 804 into misalignment, while fixing the base 802 to the cover 806 to maintain integrity of the anchor 800. Pressing the base 802 into the cover 806, against the bias of the spring 812, aligns the through holes 810 of the cover 806 with the passageway 804 of the base 802. The lead 512 can then be loaded through the holes 810 and the passageway 804, as illustrated in FIG. 26. Release of the anchor 800 allows the spring 812 to push the base 802 and cover 806 apart, wherein the lead 512 is held in place by the misalignment of the holes 810 and passageway 804. The tortuous path of the lead 512 can be adjusted by at least the strength of the spring 812 (e.g. the retention force applied to lead 512 can be determined and/or adjusted by the strength of spring 812).

It may be appreciated that one or more surface portions of the anchor 800 which contact the lead 512 may be modified to increase retention force. These surfaces may include portions of the passageway 804 and/or portions of the through holes 810 which contact the lead 512. Such surfaces may be textured, have a higher coefficient of friction, such as a soft durometer silicone, and/or include gripping features such as barbs. These gripping features may be unidirectional and/or bidirectional gripping elements.

If desired, the anchor 800 can then be disengaged from the lead 512 by pressing the base 802 into the cover 806 again so as to re-align the through holes 810 of the cover 806 with the passageway 804 of the base 802 (e.g. eliminating or at least reducing the retention force applied to lead 512). The anchor 800 can then be moved along the lead 512 to any desired location. The anchor 800 is then released to lock it in place along the lead 512. The anchor 800 can be repositioned as many times as desired.

Figure 27:
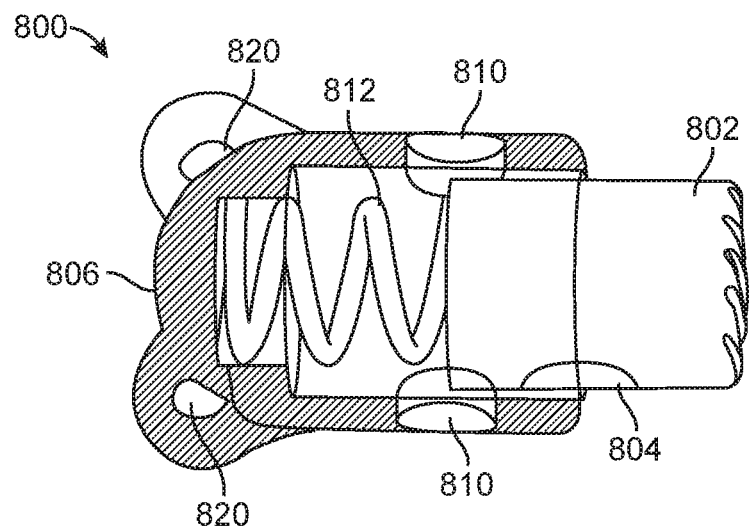
Figure 28:
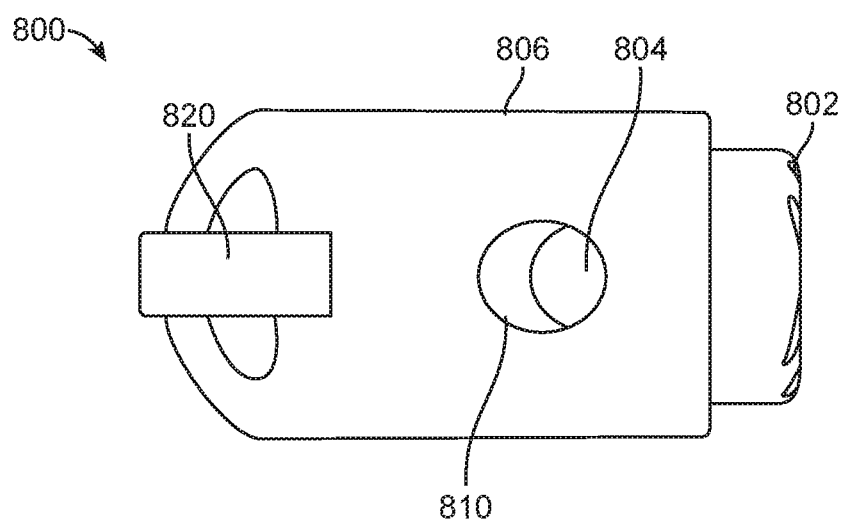

Once, the anchor 800 is desirably fixed to the lead 512, the anchor 800 is then attached to the surrounding tissue. In some embodiments, the anchor 800 includes one or more suture retention holes or eyelets to receive suture. FIG. 27 illustrates an embodiment of an anchor 800 having suture retention eyelets 820 built into the cover 806. The suture can be wrapped through the eyelets 820 to tie the anchor 800 to the tissue. FIG. 28 provides a side view of the anchor 800 of FIG. 27.

Figure 29:
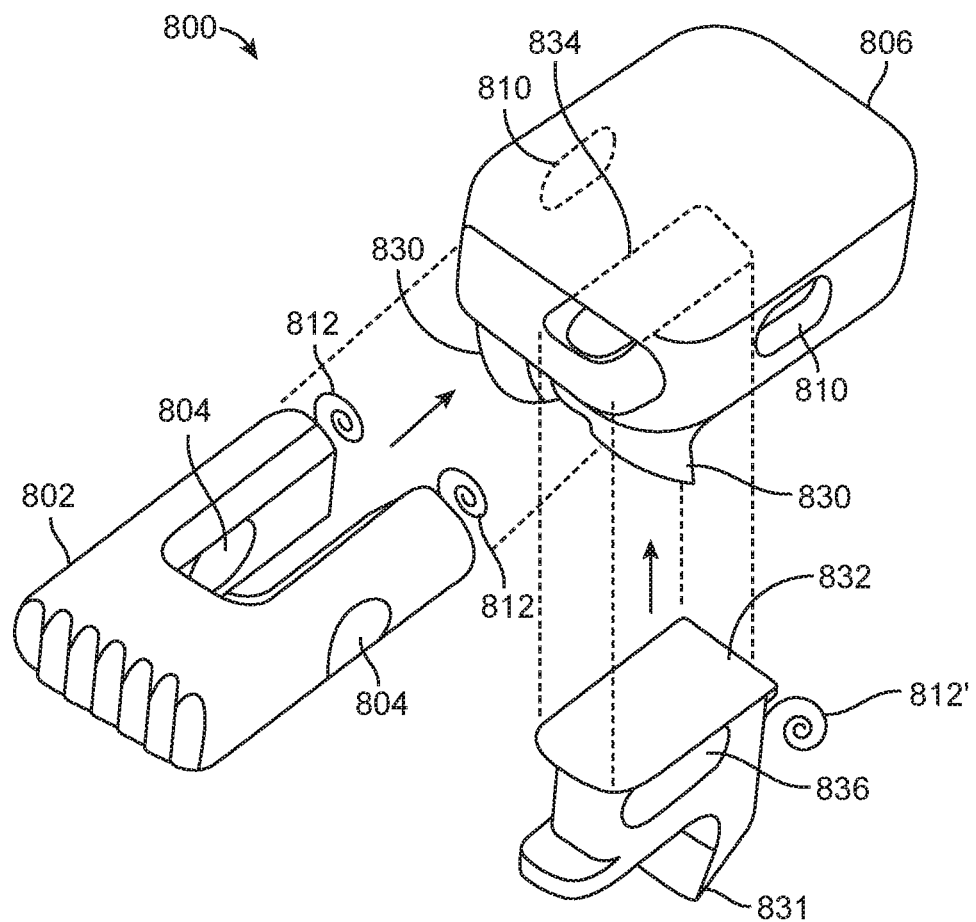
FIGS. 29, 30, 31 illustrate an embodiment of an anchor comprised of three components which slide in relation to each other to lock the anchor onto a lead and the anchor to the surrounding tissue.
Figure 30:
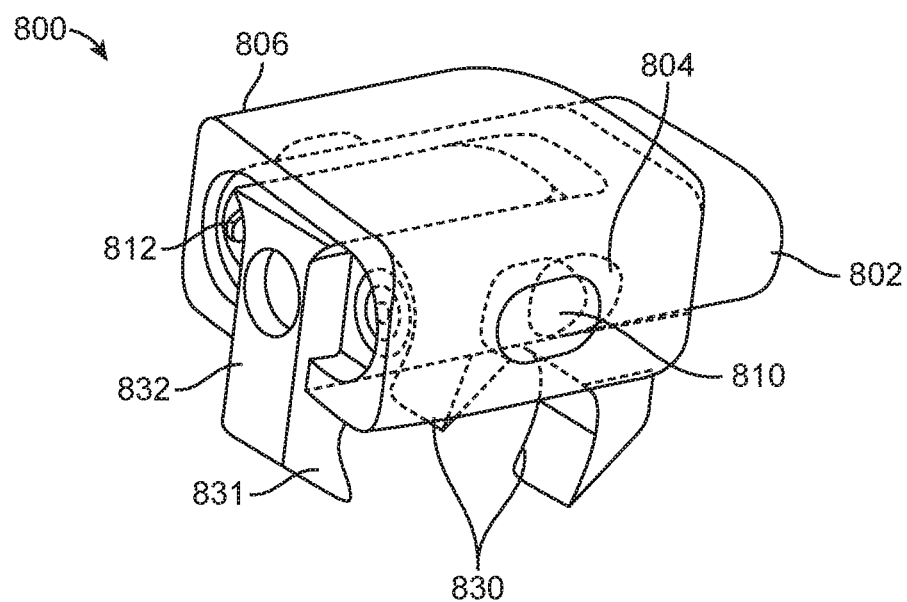

In some embodiments, the anchor 800 has tissue engagement elements (e.g. tissue grabbing jaws) which engage anchor 800 with tissue, such as to eliminate the need for suturing. In such embodiments, the anchor 800 may include an additional compression spring which controls the clamping force of the tissue grabbing jaws separately from the jaws which hold the lead. FIG. 29 illustrates an embodiment of an anchor 800 having tissue grabbing jaws. In this embodiment, the anchor 800 is comprised of three components which slide in relation to each other to lock the anchor 800 onto the lead, and secure the anchor 800 to the surrounding tissue. Again, a first component comprises a base 802 having a lumen, passageway 804, for positioning a lead therethrough or therein. A second component comprises a cover 806 which extends at least partially over the base 802. In this embodiment, the cover 806 includes at least two through holes 810 which are alignable with the passageway 804 when cover 806 is positioned around base 802. The cover 806 also includes at least one tissue engagement element, tissue grabbing jaw 830, which extends from the bottom of the cover 806. In this embodiment, the jaw 830 comprises a pointed protrusion or spike, each spike directed inwardly toward the center of the cover 806. A third component comprises an insert 832 which is insertable into the cover 806 and mateable with the base 802. The insert 832 is shaped so as to fit through an opening, passageway 834, in the bottom of the cover 806, as indicated in FIG. 29. The insert 832 includes a passageway 836 which is alignable with the through holes 810 of the cover 806 and the passageway 804 of the base 802. The insert 832 also includes at least one tissue grabbing jaw 831. In this embodiment, the jaw 831 comprises a pointed protrusion or spike. The insert 832 is configured so that when it is inserted into the cover 806, the tissue grabbing jaws 830, 831 face each other and are able to grab tissue therebetween. FIG. 30 illustrates the anchor 800 of FIG. 29 assembled, with a cross-section and transparent view.

In this embodiment, the three components are held together in a biased configuration by various springs. The anchor 800 includes at least one spring 812 which biases the base 802 and the cover 806 apart. FIG. 29 illustrates two springs 812, each located on a portion of the base 802. It may be appreciated that these springs 812 are attached to the cover 806 but have been drawn separated for clarity. In addition, the anchor 800 includes at least one spring 812' which biases the insert 832 and the cover 806 apart and the insert 832 toward the base 802. Thus, FIG. 29 illustrates the spring 812' located along a portion of the insert 832 so that the springs 812, 812' work in the same direction. The springs 812, 812' have the same or differing compression strength. Differing compression strengths allow the anchor 800 to have differing or independent strengths in locking onto the lead and grabbing onto the surrounding tissue. In some embodiments, spring 812' has a stronger compression strength than spring 812. This difference provides a stronger tissue gripping strength than lead fixating strength, which may allow for more protection of the lead body from impingement or damage by the anchor while providing more robust fixation of the anchor to the surrounding tissue.

Figure 31:
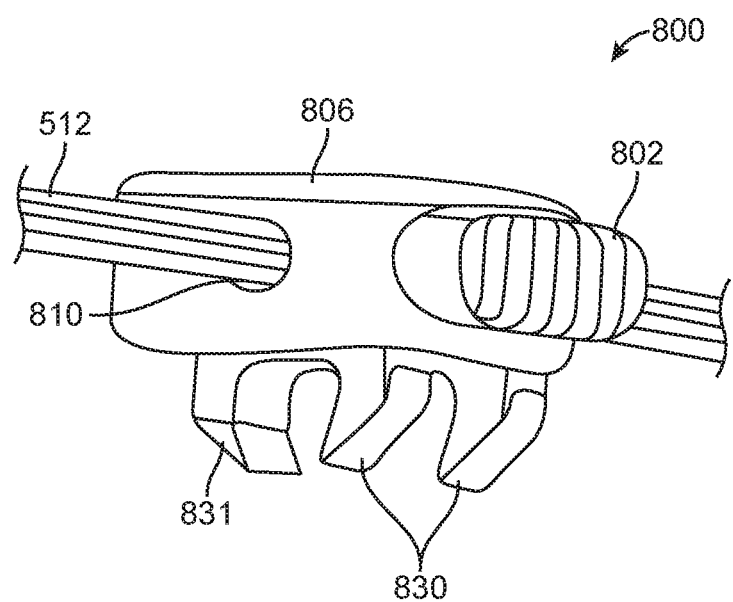

In this embodiment, the anchor 800 is actuated by pressing the base 802 and insert 832 into the cover 806, against the bias of the springs 812, 812'. This actuation aligns the through holes 810 of the cover 806 with the passageway 804 of the base 802 and the passageway 836 of the insert 832. The lead 512 can then be loaded through the holes 810 and the passageways 804, 836 as illustrated in FIG. 31. Release of the anchor 800 allows the springs 812, 812' to push the base 802, insert 832 and cover 806 apart, wherein the lead 512 is held in place by the misalignment of the holes 810 and passageways 804, 836. This frictional hold on the lead 512 can be adjusted by at least the strength of the spring 812. It may be appreciated that the surfaces of the anchor 800 which contact the lead 512 may be modified to increase retention force. These surfaces may include portions of the passageways 804, 836 and/or portions of the through holes 810 which contact the lead 512. Such surfaces may be textured, have a higher coefficient of friction, such as a soft durometer silicone, and/or include gripping features such as barbs. These gripping features may be unidirectional or bidirectional.

Figure 32:
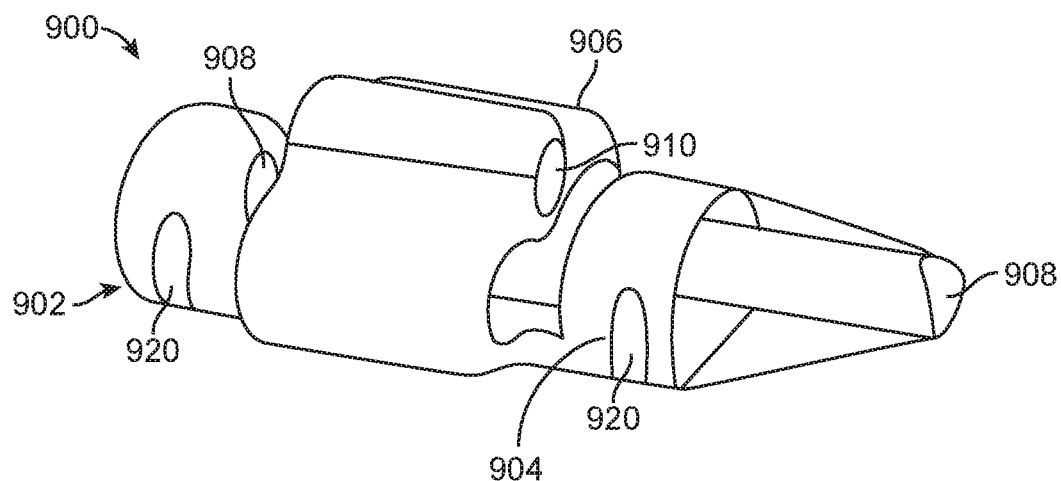
FIGS. 32, 33, 34, 35 illustrate an embodiment of an anchor comprised of an anchor body having a base portion and at least one off-set portion, wherein the off-set portion is moved to hold a lead in place by friction of the tortuous path through the lumens.

FIG. 32 is a perspective illustration of an embodiment of an anchor 900 which locks onto an elongate device, such as a lead. In this embodiment, the anchor 900 is comprised of an anchor body 902 having a base portion 904 and at least one off-set portion 906. The base portion 904 has a lumen 908 extending therethrough and the off-set portion 906 has a lumen 910 extending therethrough, wherein the lumens 908, 910 are alignable by movement of the off-set portion 906 so to receive the lead (e.g. the lead can be passed through both lumens 908,910 when they are aligned). Once the anchor 900 has been desirably positioned along the lead, the off-set portion 906 is moved to misalign the lumens 908, 910, holding the lead in place by friction of the tortuous path through the lumens 908, 910.

Figure 33:
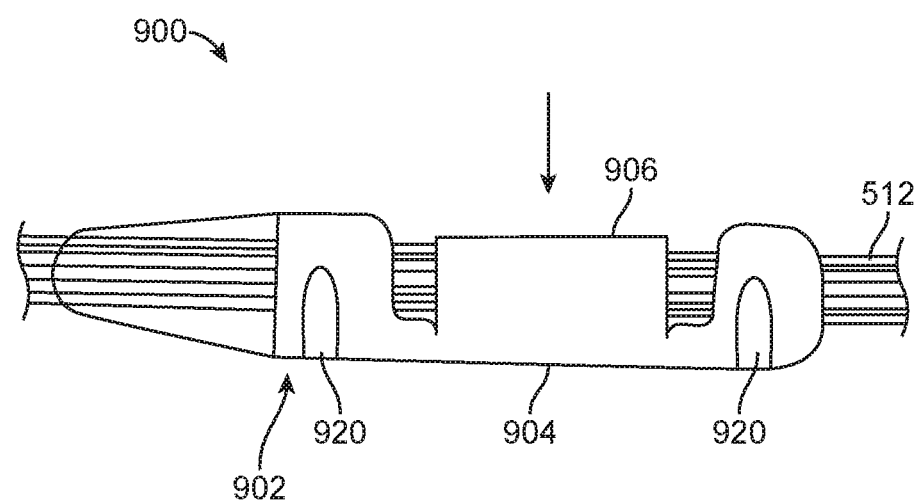
Figure 34:
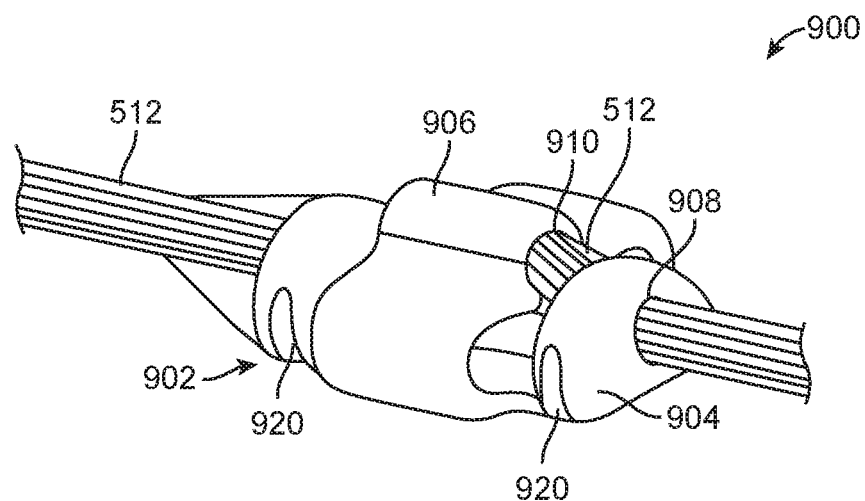
Figure 35:
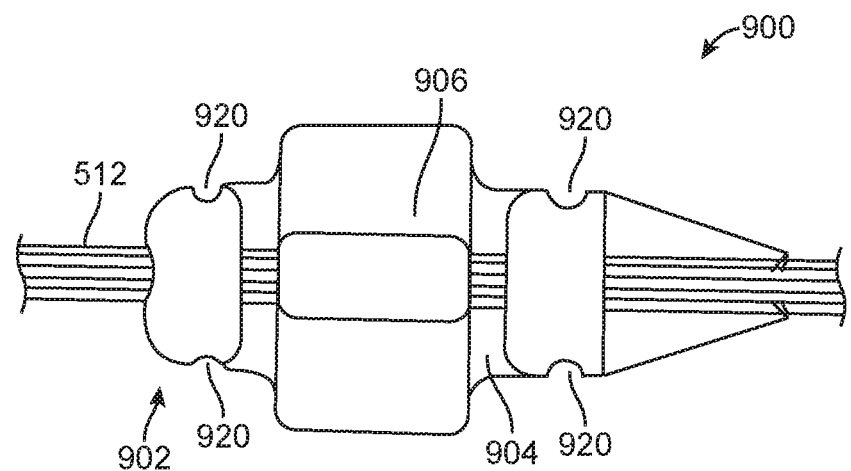

In this embodiment, the anchor body 902 can be comprised of a flexible material, such as an elastic, resiliently biased and/or shape-memory material. The anchor body 902 is a single component construction wherein the base portion 904 forms the foundation of the anchor body 902 and an off-set portion 906 extends upwards from the base portion 904 in an arch shape. Since the off-set portion 906 is flexible, the off-set portion 906 may be pressed down, toward the base portion 904 (as indicated by arrow), to align the lumens 908, 910 and allow insertion of the lead 512 therethrough, as illustrated in FIG. 33. In this configuration, the anchor body 902 can slide along the lead 512 until it is desirably positioned. Once it is desirably positioned, the off-set portion 906 is released. A resiliently biased material can be used to cause the off-set portion 906 to move upwards away from the base portion 904, misaligning the lumens 908, 910 and drawing a portion of the lead 512 upwards, as illustrated in FIG. 34. This creates a tortuous path for the lead 512 which holds the lead 512 in place by mechanical interference. FIG. 35 provides a top view of the lead 512 and anchor 900 of FIG. 34. It may be appreciated that the controlled tortuous lead path can be varied to define different retention forces. And, the anchor body 902 may include more than one off-set portion 906. Likewise, the tortuous lead path firmly holds the lead in place while reducing potential for lead damage.

It may be appreciated that the surfaces of the anchor 900 which contact the lead 512 may be modified to increase retention force. These surfaces may include portions of the lumen 908 and/or portions of the lumen 910 which contact the lead 512. Such surfaces may be textured, have a higher coefficient of friction, such as a soft durometer silicone, and/or include gripping features such as barbs. These gripping features may be unidirectional and/or bidirectional gripping elements. Likewise, it may be appreciated that the anchor body 902 may be constructed from more than one component. This may provide additional variation in tortuous paths and therefore variations in holding forces.

Once, the anchor 900 is desirably fixed to the lead 512, the anchor 900 is then attached to the surrounding tissue. In this embodiment, the anchor 900 includes one or more suture retention grooves 920 to receive suture. Thus, suture can be passed through tissue and wrapped around the anchor 900 without slipping. It may be appreciated that in other embodiments, the anchor 900 includes one or more suture throughholes for receiving suture. And, in other embodiments, the anchor 900 has tissue grabbing jaws which can eliminate the need for suturing.

FIGS. 36A-C are two perspective views and a top transparent view, respectively, of an embodiment of an anchor 1000 which locks onto an elongate device, such as a lead, for anchoring the lead underneath the skin of a patient as described herein. Anchor 1000 includes a strain relief, nose cone 1001, which can comprise a soft durometer material that surrounds an inserted lead 512. Nose cone 1001 can be configured to relieve strain applied to lead 512 due to flexion between lead 512 and anchor 1000. Anchor 1000 comprises an anchor body 1002 including two cams, locking extensions 1005a,b shown. Locking extensions 1005a,b can each include a projection, pins 1003a,b, respectively, each of which rotatably engage holes 1008a-b, respectively, such that locking extensions 1005a,b can be rotated relative to anchor body 1002. Locking extensions 1005a,b can comprise a first portion 1006a,b, respectively, and a second portion 1007a,b, respectively. FIG. 36A shows anchor 1000 in an open configuration, such that first portions 1006a,b do no significantly engage lead 512. First portions 1006a,b are configured to be rotated from the position shown in FIG. 36A (e.g. via pinching), the rotation causing first portions 1006a,b to frictionally engage and lock lead 512 in place (relative to anchor 1000), as shown in FIGS. 36B-C (e.g. bulges in first portions 1006a-b effectively lock lead 512 in at least one direction, and a cam arm prevents movement in the opposite direction). In some embodiments, second portions 1007a,b each comprise an offset proximal end, such that the offset proximal ends are configured to extend away from anchor body 1002 when in the locked position shown in FIG. 36B-C. The offset proximal ends of second portions 1007a,b can be pinched together to transition anchor 1000 from the locked state of FIGS. 36B-C to the unlocked state of FIG. 36A. In some embodiments, anchor body 1002 includes one or more projections 1004 that extend laterally from anchor body 1002, such as to provide a pushing surface for a surgical tool (e.g. hemostats).

Figure 37A:
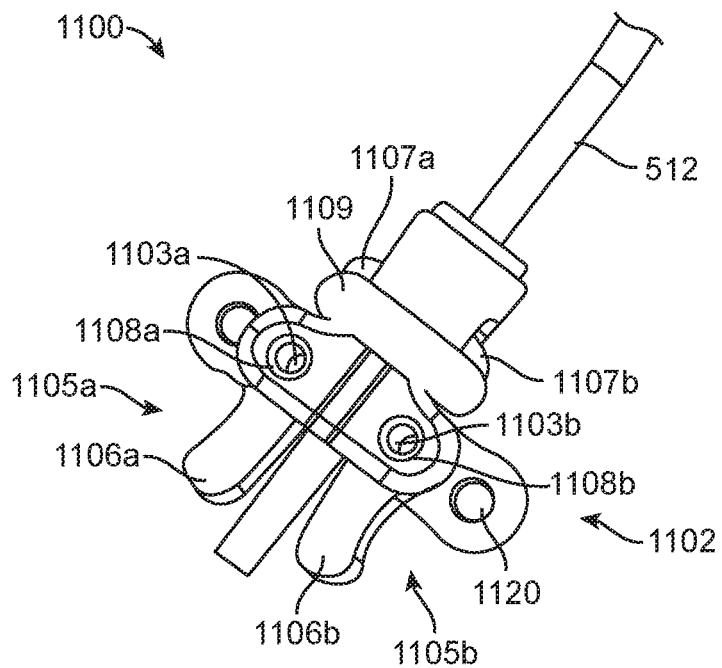
FIGS. 37A-B are a perspective view and a perspective transparent view of an anchor which locks onto an elongate device.
Figure 37B:
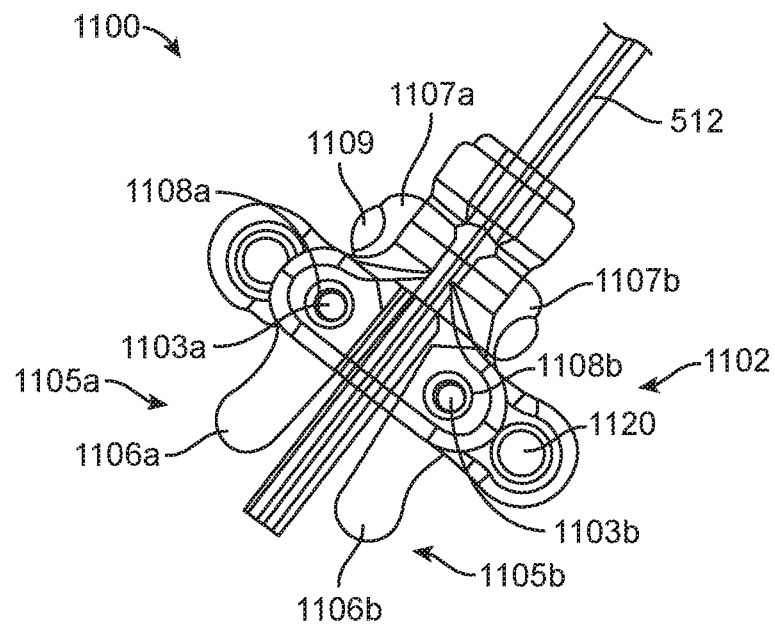

FIGS. 37A and B are a perspective view and a perspective transparent view, respectively, of an embodiment of an anchor 1100 which locks onto an elongate device, such as a lead, for anchoring the lead underneath the skin of a patient as described herein. Anchor 1100 comprises an anchor body 1102, including an O-ring 1109 and two rotatable arms, locking extensions 1105a,b shown. Locking extensions 1105a,b can each include a projection, pins 1103a,b, respectively, each of which rotatably engage holes 1008a-b, respectively, such that locking extensions 1105a,b can be rotated relative to anchor body 1102. Locking extensions 1105a,b can comprise a first portion 1106a,b, respectively, and a second portion 1107a,b, respectively. Second portions 1107a,b are constructed and arranged to receive O-ring 1109 (e.g. second portions 1107a,b include recesses constructed and arranged to receive O-ring 1109). O-ring 1109 can be configured to compress rotate locking extensions 1105a-b, such that second portions 1107a,b press against an inserted lead 512, such as to prevent movement of lead 512 relative to anchor body 1102. To allow for subsequent desired movement of lead 512, O-ring 1109 can be stretched to release (or at least reduce) the compression of first portions 1106a,b and/or second portions 1107a,b against lead 512. First portions 1106a,b and/or second portions 1107a,b can include teeth, a roughened surface, and/or other friction increasing modification configured to increase retention force with lead 512. One or more portions of locking extensions 1105a-b can be pinched together or separate apart, such as with a surgical tool (e.g. hemostats). In some embodiments, anchor body 1102 includes one or more suture retention rings 1120, such that anchor 1100 can be sutured to the patient's tissue.

Figure 38:
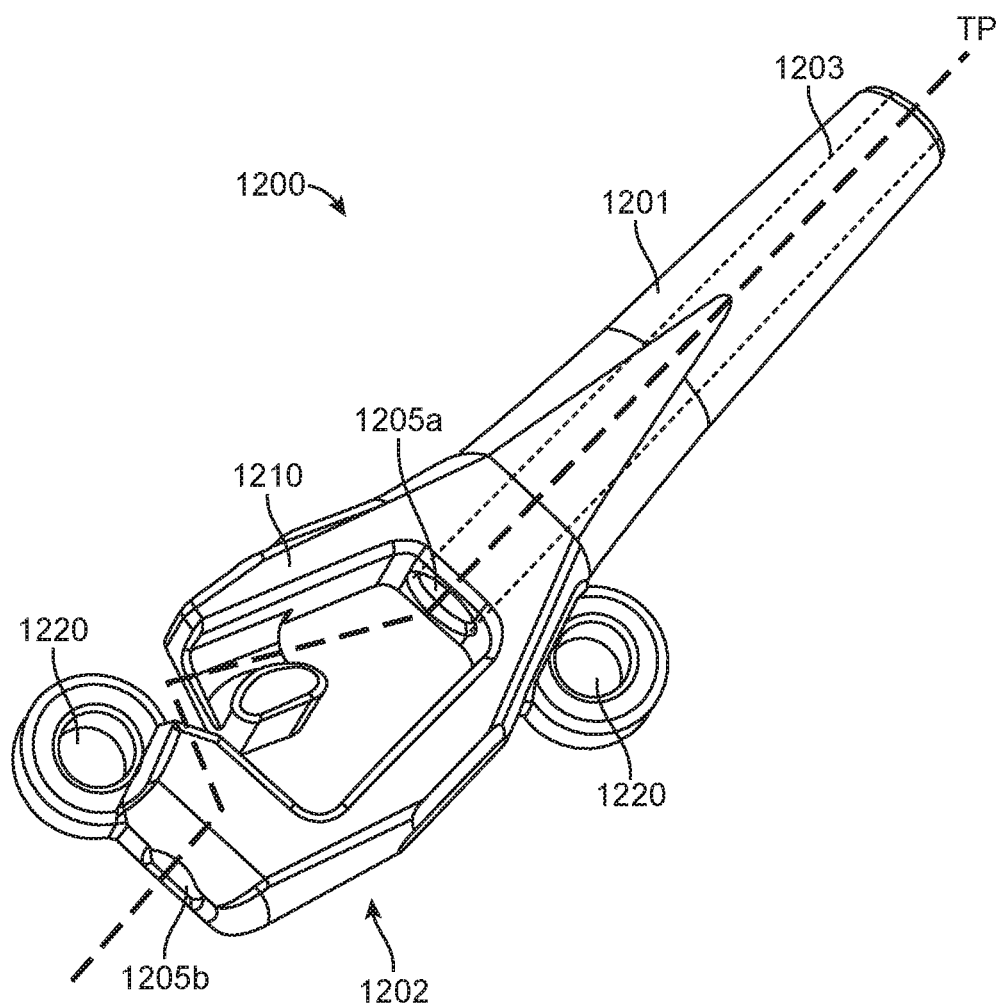
FIG. 38 is a perspective view of an anchor which locks onto an elongate device.

FIG. 38 is a perspective view of an embodiment of an anchor 1200 which locks onto an elongate device, such as a lead, for anchoring the lead underneath the skin of a patient as described herein. Anchor 1200 comprises an anchor body 1202, a conduit 1203, and a tortuous element 1210, which each include lumens or other pathways that collectively define a tortuous path TP. Anchor 1200 is constructed and arranged to slidingly receive a lead 512 (not shown) via the tortuous path TP for securing lead 512, such as when lead 512 is inserted into conduit 1203, exits opening 1205a, is advanced through tortuous element 1210, and exits 1205*b*. In some embodiments, anchor body 1202 is configured to flex or otherwise resiliently (and temporarily) deform to align tortuous element 1210 with conduit 1203 to ease insertion of lead 512. After the insertion of lead 512, anchor 1200 takes the shape shown in FIG. 38, and captures (e.g. frictionally engages) lead 512. Any portion of tortuous path TP can include teeth, a roughened surface, and/or other friction increasing modification configured to increase retention force with lead 512. Anchor body 1202 can include one or more suture retention rings 1220, such that anchor 1200 can be sutured to the patient's tissue. Anchor 1200 can include a strain relief, nose cone 1201, which can comprise a soft durometer material that surround lead 512.

Figure 39A:
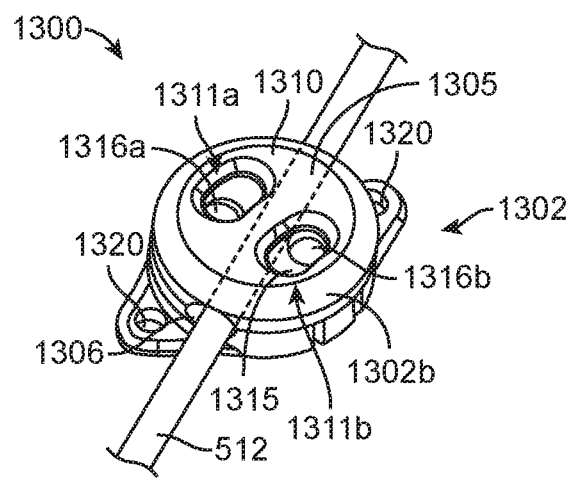
FIGS. 39A-C are a perspective view and two top transparent views, respectively, of an anchor which locks onto an elongate device.
Figure 39B:
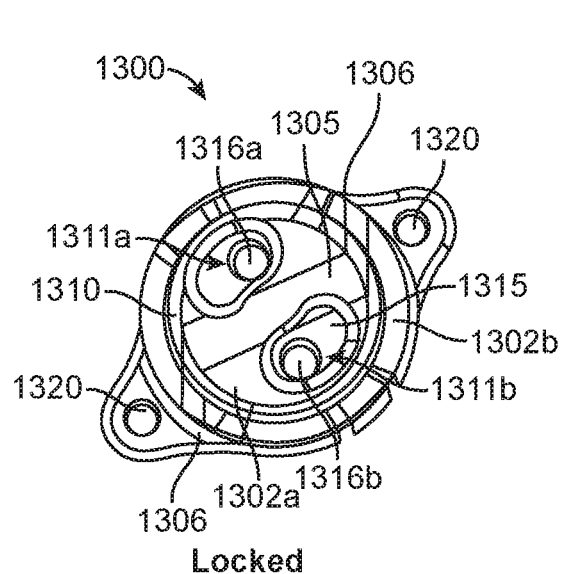
Figure 39C:
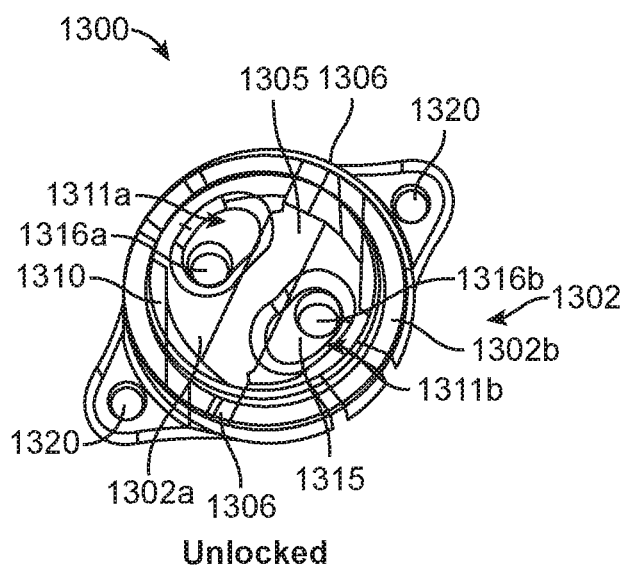

FIGS. 39A-C are a perspective view, and two top transparent views, respectively, of an embodiment of an anchor 1300 which locks onto an elongate device, such as a lead for anchoring the lead underneath the skin of a patient as described herein. Anchor 1300 comprises an inner anchor body 1302*a* surrounded by an outer anchor body 1302*b*. Inner anchor body 1302*a* includes a lumen 1305 configured to slidingly receive a lead 512 via openings 1306 of outer anchor body 1302*b*. Inner anchor body 1302*a* can be configured to rotate, such that lumen 1305 transitions from a closed (e.g. tortuous path) configuration to an open configuration position (as shown in FIGS. 39B and C, respectively). Inner anchor body 1302*a* can be sized to frictionally engage outer anchor body 1302*b*, such as to prevent undesired rotation. In some embodiments, one or more locking element are included to prevent undesired rotation. Inner anchor body 1302*a* can comprise an upper portion 1310 with one or more openings 1311, openings 1311*a,b* shown, and a lower portion 1315 with one or more recesses 1316, recesses 1316*a,b* shown. In some embodiments, openings 1311*a,b* are configured to align with, and provide access to, recesses 1316*a,b*. FIG. 39A shows anchor 1300 in the open configuration with lead 512 slidingly received by lumen 1305. FIG. 39B shows anchor 1300 in a closed configuration, such that inner anchor body 1302*a* is rotated and lumen 1305 is offset from openings 1306. In some embodiments, inner anchor body 1302*a* is rotated via a tool (not shown) that engages recesses 1316*a,b* through openings 1311*a,b*. In a closed configuration, lead 512 is compressed against anchor bodies 1302*a,b* via the offset lumen 1305 to prevent a movement of lead 512. FIG. 39C shows anchor 1300 in an open configuration, such that inner anchor body 1302*a* is rotated to a position where lumen 1305 is aligned with openings 1306. In an open configuration, the compression of lead 512 is released to allow for movement of lead 512 (e.g. removal and/or repositioning of lead 512). One or more portions of opening 1306 and/or lumen 1305 can include teeth, a roughened surface, and/or other friction increasing modification configured to increase retention force with lead 512. In some embodiments, anchor body 1302 (e.g. outer anchor body 1302*b*) includes one or more suture retention rings 1320, such that anchor 1300 can be sutured to the patient's tissue.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A tunneling tool for forming a tissue channel and/or pocket beneath a portion of skin along a body, the tunneling tool comprising:
   a distal end having a tunneling member and a guide,
      wherein the tunneling member is configured for forming the tissue channel and/or pocket beneath the portion of skin while the guide remains above the skin and indicates the location of at least a portion of the tunneling member, and
      wherein the guide is aligned with the tunneling member such that a user can determine the location of the tunneling member based on the location of one or more markings on the guide.

2. The tunneling tool according to claim 1, wherein the guide comprises a first shape, wherein the tunneling member comprises a second shape, and wherein the first shape is similar to the second shape.

3. The tunneling tool according to claim 1, wherein the guide comprises a first width, wherein the tunneling member comprises a second width, and wherein the first width is similar to the second width.

4. The tunneling tool according to claim 1, wherein the guide comprises a first width, wherein the tunneling member comprises a second width, and wherein the first width is dissimilar to the second width.

5. The tunneling tool according to claim 4, wherein the first width is less than the second width.

6. The tunneling tool according to claim 1, wherein the guide comprises a first length, wherein the tunneling member comprises a second length, and wherein the first length is similar to the second length.

7. The tunneling tool according to claim 1, wherein the guide comprises a first length, wherein the tunneling member comprises a second length, and wherein the first length is dissimilar to the second length.

8. The tunneling tool according to claim 7, wherein the first length is shorter than the second length.

9. The tunneling tool according to claim 8, wherein the tunneling member is configured to pass through the skin into the subcutaneous tissue without interference from the guide.

10. The tunneling tool according to claim 1, wherein the guide is positioned parallel to the tunneling member, and wherein the position of the guide indicates a position of the tunneling member.

11. The tunneling tool according to claim 1, wherein the tunneling member comprises a distal tip, and wherein the one or more markings indicate a distance between the markings and the distal tip of the tunneling member.

12. The tunneling tool according to claim 1, wherein the one or more markings are spaced at regular increments.

13. The tunneling tool according to claim 12, wherein the one or more markings comprise two or more markings that are spaced approximately 0.5 cm, 1.0 cm, 1.5 cm, and/or 2.0 cm apart.

14. The tunneling tool according to claim 1, wherein the one or more markings are spaced at irregular increments.

15. The tunneling tool according claim 1, wherein the tunneling tool comprises a shaft with a proximal end and a distal end, and wherein the shaft comprises a curved shape such that the proximal end is positioned higher than the distal end.

16. The tunneling tool according to claim 15, wherein the curved shape of the shaft provides clearance between a hand of a user grasping the tunneling tool and a surface of the skin when the tunneling member is inserted into the skin.

17. The tunneling tool according to claim 1, wherein a distance between the tunneling member and the guide is fixed.

18. The tunneling tool according to claim 1, wherein a distance between the tunneling member and the guide is adjustable.

19. The tunneling tool according to claim 1, wherein the tunneling member comprises a distal end including a mount, and wherein the mount is configured to rotate about the distal end.

20. The tunneling tool according to claim 19, wherein the mount rotates about the distal end between a stored position and a receiving position.

21. The tunneling tool according to claim 20, wherein the stored position comprises the mount disposed within the tunneling member.

22. The tunneling tool according to claim 20, wherein the receiving position comprises the mount extending from the tunneling member.

23. The tunneling tool according to claim 1, wherein the tunneling member comprises a distal tip including a round shape.

24. The tunneling tool according to claim 1, wherein the tunneling member comprises a distal tip including a pointed shape.

25. The tunneling tool according to claim 24, wherein the pointed distal tip comprises a blade.

26. The tunneling tool according to claim 1, wherein the guide comprises an open window.

27. The tunneling tool according to claim 1, wherein the tunneling tool comprises a storage receptacle for receiving and storing the guide.

28. The tunneling tool according to claim 1, wherein the tunneling member comprises an enlarged distal end.

* * * * *